(12) United States Patent
Hunter et al.

(10) Patent No.: US 8,702,962 B1
(45) Date of Patent: *Apr. 22, 2014

(54) CARBON DIOXIDE GAS SENSORS AND METHOD OF MANUFACTURING AND USING SAME

(75) Inventors: Gary W. Hunter, Oberlin, OH (US); Jennifer C. Xu, Olmsted Township, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 1195 days.

This patent is subject to a terminal disclaimer.

(21) Appl. No.: 12/195,358

(22) Filed: Aug. 20, 2008

Related U.S. Application Data

(63) Continuation-in-part of application No. 11/754,255, filed on May 25, 2007, now Pat. No. 8,052,854.

(51) Int. Cl.
 *G01N 27/407* (2006.01)
(52) U.S. Cl.
 USPC .......... 205/784; 204/424; 204/426; 73/23.31; 73/23.32
(58) Field of Classification Search
 USPC .......... 204/400, 421–431, 410, 411; 205/784, 205/781, 783.5–785, 787; 427/58; 73/23.31, 23.32
 See application file for complete search history.

(56) References Cited

U.S. PATENT DOCUMENTS

| | | | |
|---|---|---|---|
| 4,900,405 A * | 2/1990 | Otagawa et al. | ............. 205/781 |
| 5,194,134 A | 3/1993 | Futata et al. | |
| 5,322,601 A | 6/1994 | Liu et al. | |
| 5,520,753 A | 5/1996 | Hunter | |
| 5,668,301 A | 9/1997 | Hunter | |
| 5,736,028 A | 4/1998 | Hjortsberg et al. | |
| 5,871,633 A | 2/1999 | Greenblatt et al. | |
| 6,027,954 A | 2/2000 | Hunter | |
| 6,291,838 B1 | 9/2001 | Hunter | |

(Continued)

OTHER PUBLICATIONS

Yao, Sheng et al., "Solid Electrolyte CO2 Sensor Using Binary Carbonate Electrode", Chemistry Letters, 1990, pp. 2033-2036, The Chemical Society of Japan.

(Continued)

*Primary Examiner* — Jennifer Dieterle
(74) *Attorney, Agent, or Firm* — Robert H. Earp, III

(57) ABSTRACT

A gas sensor comprises a substrate layer; a pair of interdigitated metal electrodes, said electrodes include upper surfaces, the electrodes selected from the group consisting of Pt, Pd, Au, Ir, Ag, Ru, Rh, In, Os, and their alloys. A first layer of solid electrolyte staying in between electrode fingers and partially on said upper surfaces of said electrodes, said first layer selected from NASICON, LISICON, KSICON and β"-Alumina. A second layer of metal carbonate(s) as an auxiliary electrolyte engaging said upper surfaces of the electrodes and the first solid electrolyte. The metal carbonates selected from the group consisting of the following ions $Na^+$, $K^+$, $Li^+$, $Ag^+$, $H^+$, $Pb^{2+}$, $Sr^{2+}$, $Ba^{2+}$, and any combination thereof. An extra layer of metal oxide selected from the group consisting of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, $HfO_3$ or other metal oxide and their mixtures residing above and in engagement with the second electrolyte to improve sensor performance and/or to reduce sensor heating power consumption.

21 Claims, 17 Drawing Sheets

(56) References Cited

U.S. PATENT DOCUMENTS

| | | | |
|---|---|---|---|
| 6,763,699 | B1 | 7/2004 | Hunter et al. |
| 7,001,495 | B2 | 2/2006 | Essalik et al. |
| 7,389,675 | B1 | 6/2008 | Hunter et al. |
| 8,052,854 | B1 * | 11/2011 | Hunter et al. ............. 204/426 |
| 2003/0024814 | A1 | 2/2003 | Stetter |
| 2004/0158410 | A1 | 8/2004 | Ono et al. |
| 2006/0091010 | A1 | 5/2006 | Komatsu et al. |

OTHER PUBLICATIONS

Miura, Noiro et al., "Solid-state amperometric NO2 sensor using a sodium ion conductor", Sensors and Actuators B, 1996, pp. 124-129, 35-36, Elsevier Science S. A.

Yang, Yinbao et al. "Development of a NASICON-based amperometric carbon dioxide sensor", Oct. 6, 1998, pp. 30-34, 62, Elsevier Science S.A.

Ward, B. J. et al. "Novel processing of NASICON and sodium carbonate/barium carbonate thin and thick films for a CO2 microsensor " 2003, pp. 4289-4292, 38, Kluwer Academic Publishers.

Xu, J. C. "Miniaturized thin film carbon dioxide sensors" Apr. 21, 2004, American Ceramic society meeting, Indianapolis , IN.

Hunter, G.W. et al. "Microfabricated Chemical Sensors for Aerospace Applications", The MEMS Handbook Second Edition: Design and Fabrication, 2006, Chapter 11. 57 pages, CRC Press.

Hunter, G.W. et al. "Miniature Solid Electrolyte Carbon Dioxide Sensors", ECS 210th Meeting, Abstract 2117, May 26, 2006, http://www.electrochem.org/meetings/scheduler/abstracts/210/2117.pdf.

Hunter, G.W. "Miniaturized Sensor Systems for Aerospace Fire Detection Applications " Sep. 2004.

Kida, T. et al. "Stability of Nasicon-based CO2 sensor under humid conditions at low temperature", Sensors and Actuators B, Jan. 12, 2001, pp. 179-187, vol. 75., Elsevier Science B. V.

Hunter, Gary W. et al. "Chemical Sensors Based on Metal Oxide Nanostructures". ECS Transactions, 3 (9) p. 199-209, (2006).

Xu, Jennifer C. et al. "Novel Carbon Dioxide MicroSensor Based on Tin Oxide Nanomaterial Doped with Copper Oxide", 2 pages IEEE Journal, May 21, 2008.

* cited by examiner

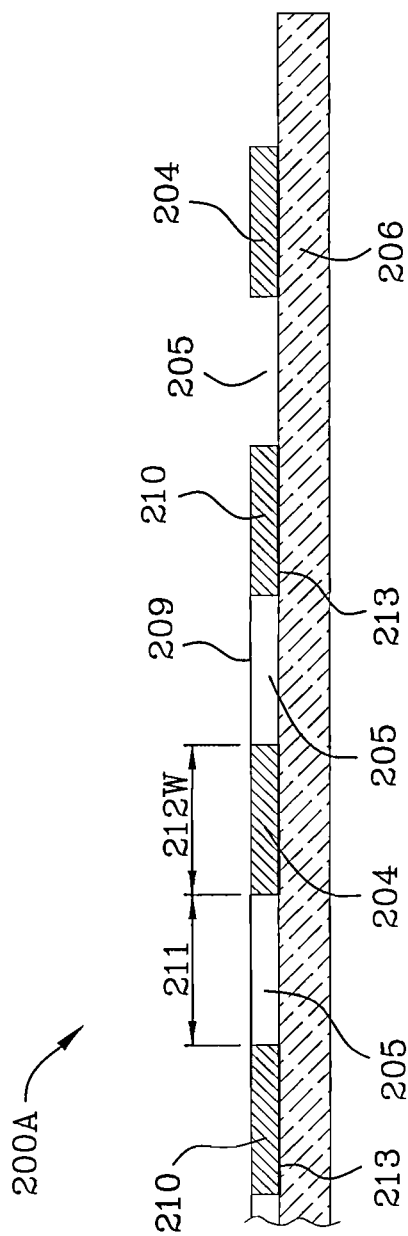
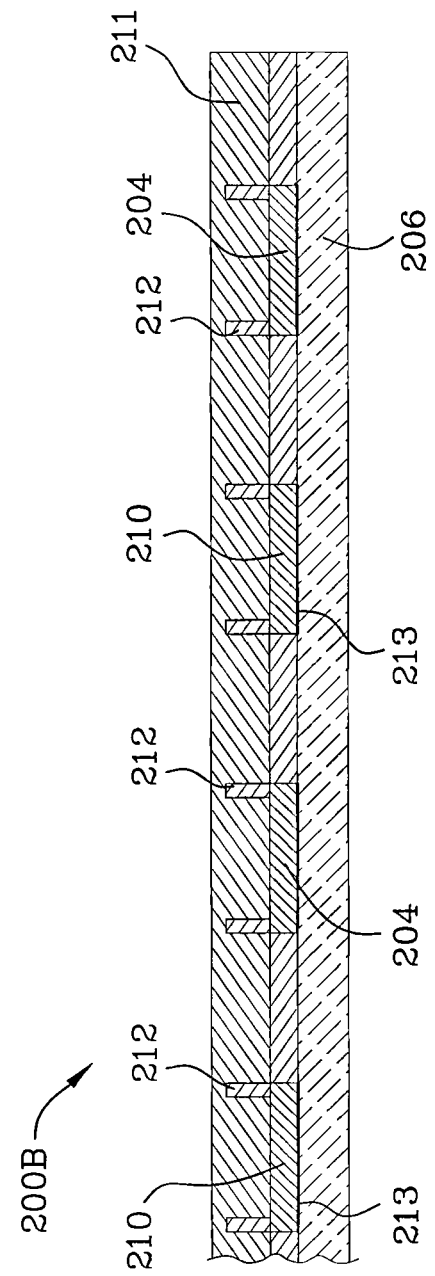

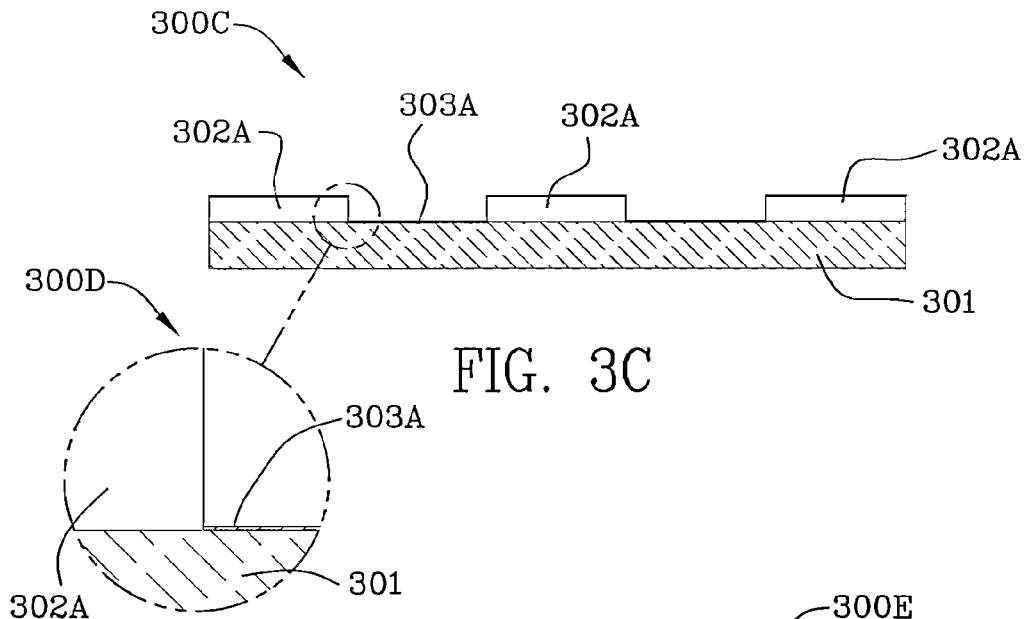
FIG. 3C
FIG. 3D
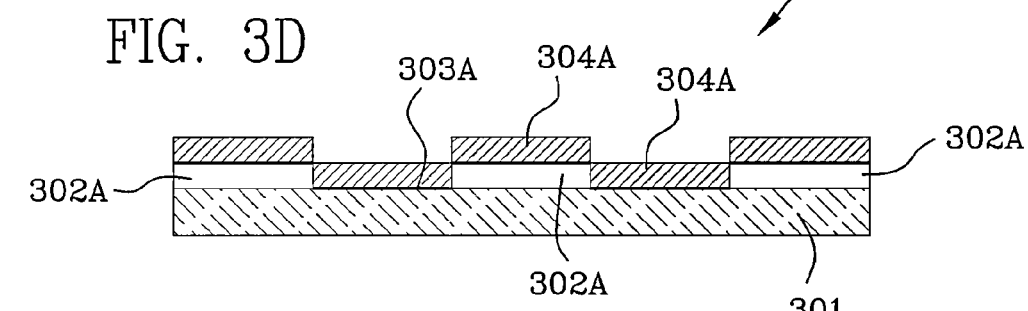
FIG. 3E
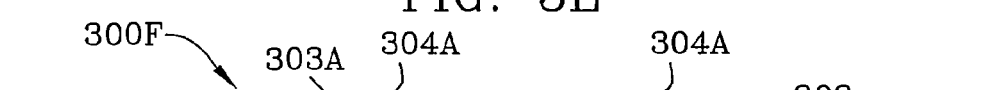
FIG. 3F
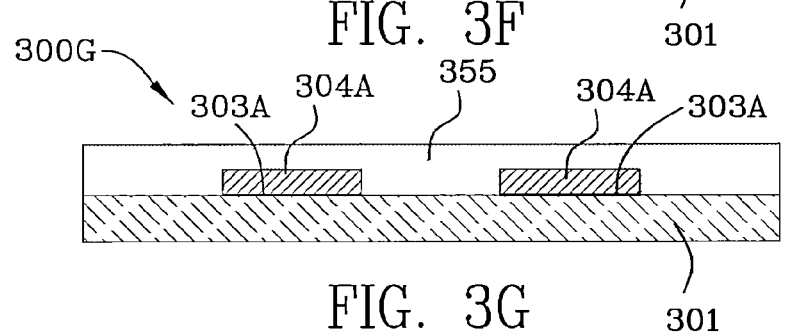
FIG. 3G

FIG. 3"O"

CARBON DIOXIDE GAS SENSORS AND METHOD OF MANUFACTURING AND USING SAME

This United States Patent application is a continuation in part of U.S. patent application Ser. No. 11/754,255 filed May 25, 2007 now U.S. Pat. No. 8,052,854.

ORIGIN OF THE INVENTION

The invention described herein was made by employees and by employees of a contractor of the United States Government, and may be manufactured and used by the government for government purposes without the payment of any royalties therein and therefore.

FIELD OF THE INVENTION

The invention is in the field of carbon dioxide gas sensors.

BACKGROUND OF THE INVENTION

The detection of $CO_2$ is essential for a range of applications including reduction of false fire alarms, environmental monitoring, and engine emission monitoring. For example, traditional smoke detectors monitoring particles can have false fire alarm rates as high as 1 in 200 in aircraft applications. Alternatively, monitoring the change of CO and $CO_2$ concentrations and their ratio ($CO/CO_2$) can be used to detect the chemical signature of a fire. Electrochemical $CO_2$ sensors which use super ionic conductors (such as Na Super Ionic Conductor or NASICON) as the solid electrolyte, and auxiliary electrolytes (such as $Na_2CO_3/BaCO_3$) have great potential for in-situ fire detection and other applications. In recent years, there has been a significant effort to develop bulk and miniaturized electrochemical $CO_2$ sensors. Compared to bulk material and thick film solid electrolyte $CO_2$ sensors, miniaturized sensors fabricated by microfabrication techniques generally have the advantages of small size, light weight, low power consumption, and batch fabrication.

Four factors are typically cited as relevant in determining whether a chemical sensor can meet the needs of an application, namely, sensitivity, selectivity, response time and stability. Sensitivity refers to the ability of the sensor to detect the desired chemical species in the range of interest. Selectivity refers to the ability of the sensor to detect the species of interest in the presence of interfering gases which also can produce a sensor response. Response time refers to the time it takes for the sensor to provide a meaningful signal. By meaningful signal it is meant that the signal has reached, for example, 90% of the steady state signal when the chemical environment experiences a step change. Stability refers to the degree which the sensor baseline and response are the same over time. It is desirable to use a sensor that will accurately determine the species of interest in a given environment with a response large and rapid enough to be of use in the application and whose response does not significantly drift over its operational lifetime.

Current bulk or thick film solid electrolyte carbon dioxide sensors have the disadvantages of being large in size, high in power consumption, difficult in batch fabrication, and high in cost. The carbon dioxide sensor design described herein has the advantage of being simple to batch fabricate, small in size, low in power consumption, easy to use, and fast responding.

FIG. 1A is a cross-sectional schematic illustration 100 of a prior art bulk carbon dioxide gas sensor. Referring to FIG. 1A, reference numeral 101 is an electrolyte known as NASICON which is an acronym or partial acronym for $Na_3Zr_2Si_2PO_{12}$ and is oriented between a platinum (paste) 103 and a Sodium Carbonate/Barium Carbonate ($Na_2CO_3/BaCO_3$) layer 102. A reference electrode 105 engages the platinum paste and a gold working electrode 104 resides in contact with the interface of the Sodium Carbonate and/or Barium Carbonate ($Na_2CO_3/BaCO_3$) 102 and the NASICON 101. By Sodium Carbonate and/or Barium Carbonate ($Na_2CO_3/BaCO_3$), it is meant that either Sodium Carbonate ($Na_2CO_3$) or Barium Carbonate ($BaCO_3$), or their mixtures may be used. The sensor is supported by quartz glass tubes (insulators) 106 for reference gases.

FIG. 1 is a cross-sectional schematic illustration 100 of a prior art gas sensor disclosing an Alumina substrate 107, interdigitated Platinum metal electrodes 108, a first solid electrolyte, NASICON 109, between the electrodes, and Sodium Carbonate and/or Barium Carbonate ($Na_2CO_3/BaCO_3$) 110 covering the NASICON and the electrodes. The first solid electrolyte is selected from the group consisting of NASICON, LISICON, KSICON, and β"-Alumina (beta prime-prime alumina in which when prepared as an electrolyte is complexed with a mobile ion selected from the group consisting of $Na^+$, $K^+$, $Li^+$, $Ag^+$, $H^+$, $Pb^{2+}$, $Sr^{2+}$ or $Ba^{2+}$). By Sodium Carbonate and/or Barium Carbonate ($Na_2CO_3/BaCO_3$), it is meant that either a material containing Sodium Carbonate ($Na_2CO_3$), Barium Carbonate ($BaCO_3$), or a mixture of Sodium Carbonate and Barium Carbonate may be used. An important feature of electrochemical cells of this type are the three-contact boundaries seen in 100. It is the intersection of 108, 109, and 110. These contacts significantly determine the effectiveness of the sensor and their number and surface area should be maximized. The inventors of the instant patent application disclosed this structure in a conference in Lisbon, Portugal in 2004 and this structure was illustrated or described in an FAA website thereafter. This structure is a schematic and not ideally achievable for a number of reasons. First, to obtain the structure exactly as illustrated in FIG. 1 a perfectly sized and aligned mask is necessary. In other words the width of the mask and its apertures has to be absolutely perfect and the alignment has to be absolutely perfect to achieve uniform three-point contact along the joint of the metal electrodes, NASICON and Sodium Carbonate/Barium Carbonate ($Na_2CO_3/BaCO_3$). Statistically, given manufacturing tolerances the structure depicted in FIG. 1 is very difficult to achieve. Photolithographic masks are aligned by hand with the aid of an electron microscope. Any misalignment of the photolithographic mask will result in photoresist trapped between NASICON and electrode finger and therefore result in a failed sensor. Simply put, the structure of FIG. 1 is very difficult to manufacture exactly as shown. Errors in manufacturing probably will result in a failed structure such as that depicted in FIG. 5D. One of the innovations of the instant invention is to realize the advantages of not having to perfectly duplicate the structure of FIG. 1, which represents the structure obtained using standard procedures of microfabrication engineers.

Previously, most solid electrolyte $CO_2$ sensors developed were bulk sized or thick film based as illustrated in FIG. 1A, which involves complicated fabrication process of hot press or screen printing. The power consumption of these sensors is very high and batch fabrication is very difficult. Porous electrodes are typical: Electrodes formed by the thick film technique are not sufficiently porous. Using a non-porous electrode can lead to the formation of sodium carbonate $Na_2CO_3$ which hinders the working electrode. The formation and dissociation of sodium carbonate $Na_2CO_3$ at the electrodes results in slower response time.

Most often (in the prior art) two sensing materials were used in a solid electrolyte $CO_2$ sensor structure. In the effort to miniaturize a $CO_2$ sensor, the standard approach was to first deposit one sensing electrolyte on the substrate, the electrodes were then deposited on top of the electrolyte, and finally the auxiliary electrolyte was deposited on the electrodes. Humidity, liquid chemical processing, and/or physical vibration tends to erode or loosen the electrolyte underneath the electrodes. This structure limited the application of standard microprocessing techniques one might employ such as photolithography. These properties limited the miniaturization of the sensor using this structure, because the electrodes could only be deposited by a shadow mask, which usually produces electrodes with less integrity when the feature is very small. That is one reason few stable and functional miniaturized sensors of this type exist.

Photolithography is used in device fabrication processes every time a pattern is transferred to a surface. It allows ion implantation or etching of a material in selected areas on the wafer (substrate). Photoresist is a photosensitive organic substance which is a sticky liquid with high viscosity which is typically spun onto a wafer and then thermally hardened in an oven. Photoresist may be positive or negative. When positive photoresist is exposed to light it breaks down long-chain organic molecules into shorter chain molecules which can be dissolved by a chemical solution called a developer. When negative photoresist is exposed to light it induces cross-linking of organic molecules such that a high atomic mass is achieved by producing longer-chain molecules. In the example of longer chain molecules, an appropriate developer solution is then used to remove the resist that has not been exposed to light. The transfer of the desired patterns onto the photoresist is made using ultraviolet light exposure through a mask which is typically a quartz plate. Masks are used in two modes. Contact lithography involves overlaying the mask directly into contact with the photoresist and proximity photolithography involves spacing the mask a distance above the photoresist. The use of photolithography enables miniaturization, batch processing, and more exact duplication of a given sensor structure. Employing these techniques can fundamentally change and improve the sensors produced; a significant technical challenge is to apply these techniques for some material systems such as those used for CO2 sensor production.

SUMMARY OF THE INVENTION

A miniaturized amperometric electrochemical (solid electrolyte) carbon dioxide ($CO_2$) sensor using a novel and robust sensor design has been developed and demonstrated. Semiconductor microfabrication techniques were used in the sensor fabrication and the sensor is fabricated for robust operation in a range of environments. The sensing area of the sensor is approximately 1.0 mm×1.1 mm. The sensor is operated by applying voltage across the electrodes and measuring the resultant current flow at temperatures from 450 to 600° C. Given that air ambient $CO_2$ concentrations are ~0.03%, this shows a sensitivity range from below ambient to nearly two orders of magnitude above ambient. Sensor current output versus ln [$CO_2$ concentration] (natural logarithm of the carbon dioxide concentration) shows a linear relationship from 0.02% to 1% $CO_2$. This linear relationship allows for easy sensor calibration. Linear responses were achieved for $CO_2$ concentrations from 1% to 4% and to the logarithm of the $CO_2$ concentrations from 0.02% to 1%. These sensing measurement results, but not the method of sensor fabrication, were disclosed in the April 2004 American Ceramic Society presentation and at the Fire Prevention Conference in Lisbon November 2004. This $CO_2$ sensor has the advantage of being simple to batch fabricate, small in size, low in power consumption, easy to use, and fast response time.

One aspect of the development of the invention was to develop miniature $CO_2$ sensors for a wide variety of applications. This miniaturized $CO_2$ sensor can be integrated into a sensor array with other sensors such as electronics, power, and telemetry on a postage stamp-sized package. Like a postage stamp, the complete system ("lick and stick" technology) could be placed at a number of locations to give a full-field view of what is chemically occurring in an environment.

The development of miniature electrochemical sensors based on solid electrolytes NASICON ($Na_3Zr_2Si_2PO_{12}$) and $Na_2CO_3$/$BaCO_3$ for $CO_2$ is an important aspect of the instant invention. Semiconductor microfabrication techniques are used in the sensor fabrication. The fabrication process involves three fabrication steps: 1) deposition of interdigitated electrodes on alumina substrates; 2) deposition of solid electrolyte NASICON ($Na_3Zr_2Si_2PO_{12}$) between the interdigitated electrodes; and 3) deposition of auxiliary solid electrolytes $Na_2CO_3$ and/or $BaCO_3$ (1:1.7 molar ratio) on top of the entire sensing area. The resulting sensing area is approximately 1.0 mm×1.1 mm. The multiple interdigitated finger electrodes are in contact with the solid electrolytes and the atmosphere in multiple locations rather than in just one location as is seen with single set of electrode structures. Thus, this approach yields increased surface area associated with three-contact boundaries as compared to other sensors with similar dimensions. The same sensor structure could also be applied to develop other sensors such as NO sensors with the corresponding auxiliary electrolytes $NaNO_2$ or $NaNO_3$.

An amperometric circuit is used to detect $CO_2$. The detection system includes pairs of electrodes with constant voltage, V, applied across the electrodes.

The sensing mechanism of the amperometric $CO_2$ sensors can be understood based on the reactions taking place at the working and reference electrode of each pair of electrodes. The following two reactions may be considered to carry current between the electrodes:

Working Electrode $2Na^+ + CO_2 + \frac{1}{2}O_2 + 2e^- \rightarrow Na_2CO_3$

Reference Electrode $Na_2O \rightarrow 2Na^+ + \frac{1}{2}O_2 + 2e^-$

The reduction current is the result of the reaction taking place at the working electrode where electrons are consumed. The oxidation current is the result of the reaction taking place at the reference electrode where electrons are released. The following reaction can then be considered to be:

Overall Reaction $Na_2O + CO_2 \rightarrow Na_2CO_3$

Platinum is used as the preferred material for the electrode. However, electrodes made from other metals such as Palladium, Silver, Iridium, Gold, Ruthenium, Rhodium, Indium, or Osmium may also be used. In addition, non-porous or porous electrodes may be used The auxiliary electrolyte ($Na_2CO_3$ and/or $BaCO_3$) is deposited homogeneously on the entire sensing area of the sensor, including both the working and reference electrodes. The deposition of an auxiliary carbonate electrolyte improves the selectivity and sensitivity of the sensor to $CO_2$ gases and the flow of the desired species within the electrolyte. At the working electrode, depleted concentration of sodium ions ($Na^+$) can be recovered by the transfer of sodium ions ($Na^+$) from NASICON through the three-phase boundary of the electrodes, NASICON electrolyte, and an auxiliary electrolyte layer. The sodium carbonate, $Na_2CO_3$, deposited at the working electrode during reacting with $CO_2$ can be transferred to the reference electrode through the $Na_2CO_3/BaCO_3$ auxiliary carbonate electrolyte layer if temperatures are high enough, for example, 450-600° C.

These mechanisms allow the sensor to measure $CO_2$ but recover back to its initial state. The sensing mechanism has increased performance from the $Na_2CO_3/BaCO_3$ auxiliary carbonate electrolyte layer being distributed across both the working and the reference electrodes at high operating temperatures in the 450-600° C. The eutectic mixture of $Na_2CO_3/BaCO_3$ as the auxiliary carbonate electrolyte layer has a lower melting temperature enabling improved flow within the electrolyte at a reduced temperature range. The $Na_2CO_3/BaCO_3$ auxiliary carbonate electrolyte can act as a diffusion barrier to prevent other species from reaching the electrode/electrolyte interface and interfering with the correlation of measured current with detection of the desired chemical species.

In order to facilitate a faster response time, porous platinum electrodes can be used with an auxiliary carbonate electrolyte having an increased porosity. The sensor structure employs interdigitated electrodes which can be generally thought of as interdigitated fingers. Unique fabrication processes to miniaturize the $CO_2$ sensor are used.

A unique amperometric $CO_2$ sensor is produced using a non-standard approach as disclosed herein and has the following attributes:

First is the miniature size of the sensor with interdigitated electrodes. The fabrication of electrodes with photolithography enables the sensor to have a small sensor sizes with a sensing area of approximately 1.0 mm×1.1 mm (electrode width and spacing between electrodes is around 30-50 µm). Further miniaturization is possible and the size can be varied to control sensor properties. The sensor would be very difficult to make with a shadow mask if a layer of electrolyte is deposited before the electrodes as is the case in most other attempted processes. Interdigitated electrodes are very important for amperometric $CO_2$ sensors because the current output of the electrodes is summed and bussed which results in currents much higher compared to the traditional two electrodes with the same size. As a result, better sensitivity of the sensor is achieved. In other words for a given change of input to the sensor in terms of $CO_2$ concentration, a larger differential change in output is observed.

Secondly, the sensor has a robust structure. The interdigitated electrodes were deposited directly on the alumina substrate with strong adhesion, which will stand the attack of humidity and vibration. This is in contrast to the approach of depositing the electrolyte first on the substrate which has less inherent stability.

Thirdly, the sensor has a unique arrangement of electrodes/electrolytes. Solid electrolyte NASICON is deposited between interdigitated fingers and the auxiliary electrolyte $Na_2CO_3/BaCO_3$ was deposited on the whole sensing area, forming greater length of three-point boundaries (electrode, solid electrolyte NASICON, and auxiliary electrolyte $Na_2CO_3/BaCO_3$), which is beneficial for amperometric gas sensing. Interdigitated finger electrodes on a substrate were used as sensor structures before but only one or mixed sensing materials were deposited. The interdigitated finger electrode structure is deposited with two distinctive sensing materials forming maximum length three-point contacts. The sensor was tested continuously for at least three weeks at high temperatures showing its robust nature. The sensor structure could also be used with any other sensing system which requires two distinctive deposited materials in an electrochemical cell structure.

Finally, the sensor is very easy to batch fabricate compared to the bulk-sized sensors and consumes much less power. This is specifically due to the non-standard photolithographic approach used.

Using the process disclosed herein, sensors may be fabricated which have good sensitivity, selectivity, response time, and stability.

The carbon dioxide sensor produced by the innovative technique described herein is applicable to the fire detection (including hidden fire), EVA applications, personal health monitoring, and environmental monitoring. The sensor and its electronics are integrated into a postage stamp sized system. The low cost due to the batch fabrication process and its compact size make it highly affordable and thus useable in a wide array of locations.

A process for sensing carbon dioxide is accomplished which includes the following steps: applying a constant direct current voltage across the pair of electrodes. The electrodes are separated by an electrolyte material containing sodium, and the electrodes are located between a layer of alumina substrate and an electrolyte layer of auxiliary carbonate.

Carbon dioxide is then reacted with the material containing sodium at the first three-point boundary. The first three point boundary is located at the joinder of one of the electrodes, the electrolyte material containing sodium, and the barium containing auxiliary electrolyte.

An oxide of sodium is then reacted at a second three-point boundary. The second three-point boundary is located at the joinder of the other of the electrodes, the electrolyte material containing sodium, and a sodium/barium containing auxiliary electrolyte.

Finally, the resulting current is measured and the change in current is correlated to the concentration of carbon dioxide.

The invention includes a micro amperometric electrochemical (solid electrolyte) carbon dioxide ($CO_2$) sensor using a novel and robust sensor design. Semiconductor microfabrication techniques are used in the sensor fabrication and the sensor is fabricated for robust operation for a range of applications such as fire detection and environmental monitoring. The sensor has a sensing area of 0.99 mm by 1.10 mm and the examples disclosed in the parent application without the metal oxides covering the auxiliary electrolyte are mainly operated at 600° C. for $CO_2$ detection in an amperometric mode. Operation at 600° C. for $CO_2$ detection requires more energy for heating the sensor. The sensors operated at 600° C. have low detection limits and wide detection ranges and are considered to comprise the-state-of-art. The sensors disclosed in the parent application also include and identify certain metal oxides covering the auxiliary electrolyte. The instant continuation in part application discloses additional metal oxides which cover and engage the auxiliary electrolyte. Additionally, it is disclosed in this instant application that the metal oxides may be mixed with the auxiliary electrolyte The metal oxides provide additional electrons to the sensor system which enable operation at reduced temperatures.

Catalysts are disclosed herein which further facilitate the reactions of the carbon dioxide sensor at low temperature.

Although the sensors without the metal oxides over and engagement with the auxiliary electrolyte have low power consumption due to their small size, there is still a great desire to decrease sensor operation temperature so as to reduce its power consumption.

The solid electrolyte $CO_2$ microsensor is modified with semiconductor metal oxides. The metal semiconductors include $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$, of which some are n-type semiconductors and some are p-type semiconductors. N-type semiconductors have a surplus of electrons which are added to the sensor system and which facilitate the reduction reaction, and p-type semiconductors has a surplus of holes which are added to the sensor system to facilities the oxidation reaction at the electrodes. The addition of metal oxide sol gel on a solid electrolyte $CO_2$ sensor greatly improves the performance of the sensor. Preliminary testing results indicate that the sensor can detect $CO_2$ concentrations from 0.5% to 4% at 375° C., 2V, which is considerably lower than the traditional solid electrolyte sensor operation temperature of 600° C. which does not include the extra layer of metal oxide thereover. An amperometric solid state oxide-based electrolyte $CO_2$ microsensor operating at 375° C. with a wide detection range has been demonstrated. This $CO_2$ sensor has the advantages of being simple to batch fabricate, small in size, low in power consumption, easy to use, and which possesses and provides a fast response time.

There are a range of applications for $CO_2$ sensor technology including fire detection and environmental monitoring which strongly favor low power consumption. Application of a nanocrystalline $SnO_2$ surface coating to the solid electrolyte increases the sensor response and allows for a lower operating temperature.

This example decreases the sensor operation temperature through the use of a surface coating which supplies additional electrons for the reduction-oxidation reaction (redox reaction). By decreasing the sensor operating temperature, the power consumption is greatly reduced, which has significant importance for sensor integration and application. The design of the sensor of this example (which includes the metal oxide over and in engagement with the auxiliary electrolyte) includes one more step added to the sensor processing, that is, to coat a layer of metal oxide sol gel on top of the solid electrolytes. This coated layer selected from the group of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$, provides more electrons for the reduction reaction to detect $CO_2$ gas at the working electrode or provides more holes for the oxidation reaction of Na2O at reference electrode. The benefits of the sensors of this example include robust structure, microsize, batch fabrication, fast response, and wide detection range. The addition of the $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ sol gel also greatly improves sensor performance and decreases sensor operation temperature, and thus decreases the power consumption.

The fabrication of the carbon dioxide sensor of this example includes four steps: (1) deposition of platinum interdigitated finger electrodes on alumina substrate; (2) deposition of the NASICON solid electrolyte primarily in between the finger electrodes; (3) deposition of auxiliary electrolytes $Na_2CO_3/BaCO_3$ in a 1:1.7 molar ratio on top of the whole electrode area; and, (4) coating of the $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ sol gel on the auxiliary electrolytes.

This example of the sensor utilizes interdigitated finger electrodes and uses unique fabrication means to miniaturize the $CO_2$ sensor to microsize. Solid electrolyte (such as NASICON, $Na_3Zr_2Si_2PO_{12}$) is deposited primarily in between the electrodes; auxiliary electrolyte (such as $Na_2CO_3/BaCO_3$) stays on top of the electrodes and electrolyte; and the metal oxide selected from one or more of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ nanomaterial is finally applied on the auxiliary electrolyte surface.

The sensor with the extra layer of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ results in a unique amperometric $CO_2$ microsensor having all four of the following attributes.

First, the sensor has a robust structure. The interdigitated electrodes are deposited directly on the alumina substrate with a strong adhesion, which will stand the attack of the humidity and vibration. Deposition of the electrodes directly on the substrate is unique because heretofore in the prior art when more than one electrolyte sensing system is used in fabricating sensors, the standard approach was to first deposit one electrolyte on the substrate, then the electrodes were deposited on top of the electrolyte, and finally the auxiliary electrolytes were deposited on the electrodes. This prior art structure limited the miniaturization of the sensor, because the electrodes could only be deposited by a shadow mask, which usually produces electrodes with less integrity when the features thereof were very small. Further, humidity or physical vibration tend to erode or loosen the electrolyte underneath the electrodes and thus few stable and functional micro-sensors of this type could be produced.

Second, the miniature sensor still maintains a high signal output. The fabrication of electrodes with photolithography enables the sensor to have a small sensing area of 0.99 mm by 1.10 mm (electrode finger width and spacing between electrode fingers are 30 μm) which would be very difficult to make with a shadow mask if a layer of electrolyte is deposited before the electrodes, as performed in prior art processes. Whereas interdigitated electrodes are very important for amperometric $CO_2$ sensors because their current output is much higher compared to that of the prior art sensors having two electrodes with the same size.

Thirdly, the sensor has a unique arrangement of electrodes/electrolytes. Solid electrolyte NASICON was deposited mainly in between interdigitated fingers and the auxiliary electrolyte $Na_2CO_3/BaCO_3$ was deposited on the whole sensing area, forming the greatest length of the three-point boundaries (electrode, solid electrolyte NASICON, and auxiliary electrolyte $Na_2CO_3/BaCO_3$), which is beneficial for amperometric mode gas sensing. Adding semiconductors (metal oxides) selected alone or in combination from: $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ functions as an electron or holes feeder to facilitate the redox reaction. Previously interdigitated finger electrodes deposited directly on a substrate were used by others as sensor structures but only one or a mixed sensing material was deposited on the electrodes. Whereas using the sensor design of the present example, the interdigitated finger electrodes on the substrate can be deposited with two distinctive sensing material systems, forming a maximum three-contact boundary.

Fourth, the addition of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ nanomaterials (metal oxides, semiconductors) on the auxiliary electrolyte surface provides extra free electrons or holes to the reduction-oxidation sites to facilitate the reduction reaction for $CO_2$ detection or $Na_2O$ oxidation reaction at the three-point boundary of the working and reference electrodes. The addition of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ is the reason that the operation temperature of the solid electrolyte $CO_2$ sensor can be reduced from 600° C. to 200° C.-375° C. While the sensor has the advantage of reduced operational temperature at as low as 200-355° C. it does not lose the advantages of a simple to batch fabricate, small in size, low in power consumption, easy to use, and fast response time sensor. The addition of the $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ nanomaterials greatly decreases the heating power consumption of the sensors.

It should be noted and those skilled in the art will understand that the sensors are heated by a battery or other energy source to a temperature at which they operate. Therefore, as explained herein the addition of the $SnO_2$ enables operation of the sensor at a lower temperature thus saving energy which can be used to prolong operation of the sensor both from the standpoint of heating the sensor to an operational temperature and from the standpoint of applying a voltage across the interdigitated fingers.

The carbon dioxide sensor produced by the innovative technique described in this disclosure are applicable to the fire detection (including hidden fire), EVA applications, personal health monitoring, and environmental monitoring. The sensor and its electronics could be integrated on a postage stamp sized substrate. The low cost due to the hatch fabrication process, reduced temperature operation, and its compact size make it highly affordable and possible to be installed in a wide array of locations.

Results show that the sensor, before being coated with $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ sol gel, provides responses to $CO_2$ gases at 355° C. and 405° C. commensurate with the use of solid electrolyte sensing materials. The responses of a $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ coated sensor to $CO_2$ gases are greatly enhanced at 355° C. and testing showed responses to $CO_2$ concentrations from 0.5% to 4% were achieved at 375° C. The examples of the examples of the solid electrolyte $CO_2$ sensor which did not include use of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ did provide a wide detection range (0.02% to 2%) but the sensor had to be operated at 600° C.

The resulting semiconductor metal oxide modified $CO_2$ sensor with reduced power consumption can be further improved and integrated into a sensor array with other sensors, electronics, power, and telemetry on a postage stamp sized package. Like a postage stamp, the complete system ("lick and stick" technology) could be placed at a number of locations including some hidden areas to give a full-field understanding of what is occurring in an environment. The same sensor structure could also be applied to develop $NO_x$ or $SO_x$ sensors with the corresponding auxiliary electrolytes $NaNO_3$, or $NaSO_3$ and $NaSO_4$ respectively.

The sol-gel process is a wet-chemical technique (Chemical Solution Deposition) for the fabrication of materials (typically a metal oxide) starting from colloidal particles (sol for nanoscale particle) to produce an integrated network (gel).

BRIEF DESCRIPTION OF THE DRAWINGS

FIG. 2A is a cross-sectional schematic view taken along the lines 2A-2A of FIG. 2.

FIG. 2B is a cross-sectional view similar to FIG. 2A with first and second solid electrolytes over the substrate and the interdigitated electrodes.

FIG. 3C is a cross-sectional schematic illustration similar to FIG. 3B with a first layer of Titanium sputtered onto the substrate.

FIG. 3D is an enlargement of a portion of FIG. 3C illustrating the sputter deposition of the first layer of the Titanium over the substrate and the photoresist.

FIG. 3E is a cross-sectional schematic illustration of a second layer of Platinum deposited above the first metallization layer of Titanium and the photoresist.

FIG. 3F is a cross-sectional schematic illustration of the substrate with two interdigitated electrodes affixed to the substrate with the photoresist removed with acetone or other suitable solvent.

FIG. 3G is a cross-sectional schematic illustration of photoresist spun over the interdigitated Titanium/Platinum electrodes and the substrate.

FIG. 3O is a cross-sectional schematic similar to FIG. 3J of another example of the application of a first solid applied over the substrate, interdigitated electrodes, photoresist using sputter deposition.

The drawings will be better understood when reference is made to the Description of the Invention and Claims which follow hereinbelow.

DESCRIPTION OF THE INVENTION

Figure 2:
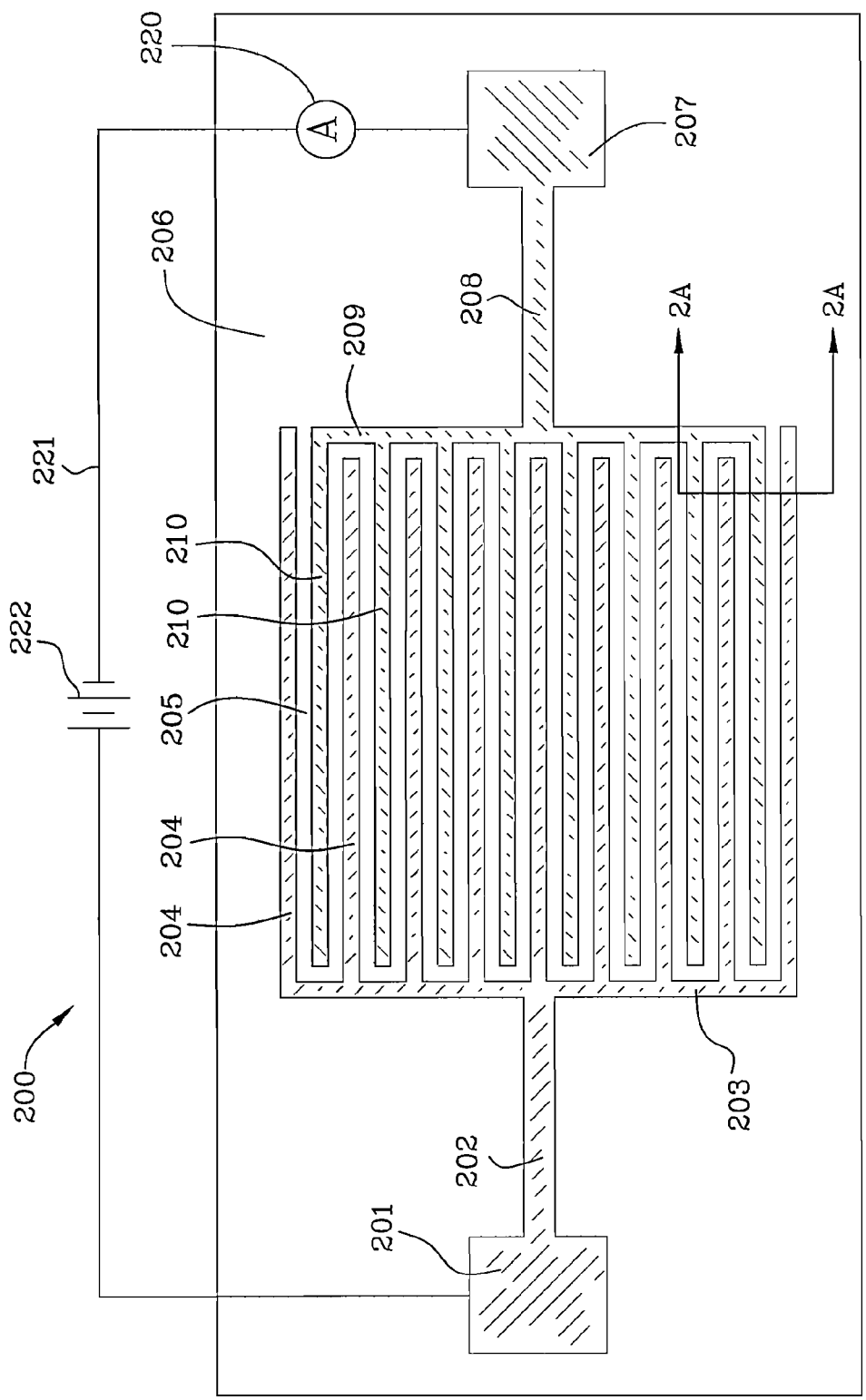
FIG. 2 is a cross-sectional schematic illustration of interdigitated electrodes residing on a substrate forming part of the sensor of the present invention.

FIG. 2 is a cross-sectional schematic illustration 200 of interdigitated electrodes 204, 210 residing on a substrate 206 forming part of the sensor of the present invention. Positive contact pad 201 is interconnected by lead 202 to positive bus 203 which is in turn interconnected with positive interdigitated positive electrodes (fingers) 204. Negative contact pad 207 is interconnected by lead 209 to negative bus 209 which in turn is interconnected with negative interdigitated negative electrodes (fingers) 210. Electrodes 204, 210 are fixedly engaged to the Alumina substrate 206. The Alumina substrate 206 is an insulator and is approximately 625 μm thick.

Still referring to FIG. 2, reference numeral 205 indicates the gap between electrodes 204, 210. The electrode width 212W and width of the gap between electrodes 211 are both around 30 μm. See FIG. 2A. Contact pads 201, 207 are interconnected by a conductor 221 to battery 222 which is nominally at 1 V DC. Amp meter 220 measures and records current in the circuit.

FIG. 2A is a cross-sectional schematic view 200A taken along the lines 2A-2A of FIG. 2. Gap 205 and electrodes 204, 210 are illustrated as is the negative bus 209. In one example illustrated herein, the width 211 of the gap 205 is approximately 30 μm. The electrodes 204, 210 have a width of approximately 30 μm as indicated by reference numeral 212W. A thin layer of Titanium 213 is beneath Platinum electrodes 204, 210. Alternatively, the electrode material may comprise a thin layer of $PtO_x$ followed by a relatively thick layer of Platinum.

FIG. 2B is a cross-sectional schematic view 200B similar to FIG. 2A with first and second solid electrolytes 212, 211 over the substrate 206 and interdigitated electrodes 204, 210. Reference numeral 212 is also used to indicate the contour of the first electrolyte, for example, NASICON, LISICON, or β"-Alumina (beta prime-prime alumina in which when prepared as an electrolyte is complexed with a mobile ion selected from the group consisting of $Na^+$, $K^+$, $Li^+$, $Ag^+$, $H^+$, $Pb^{2+}$, $Sr^{2+}$, or $Ba^{2+}$). The first electrolyte may be any number of solid electrolytes known for their conductivity performance. These electrolytes may include sodium or lithium as in the case of NASICON and LISICON, but the electrolyte is not limited to materials containing these elements and may include any number of elements including but not limited to Na, Li, K, Ag, H, Pb, Sr, or Ba. The second solid electrolyte 211 may include Sodium Carbonate ($Na_2CO_3$) or mixture of Sodium Carbonate ($Na_2CO_3$) and Barium Carbonate ($BaCO_3$). Other electrolyte materials such as $Li_2CO_3$, $K_2CO_3$, $Rb_2CO_3$, $SrCO_3$, $Ag_2CO_3$, $PbCO_3$ and their mixtures among them or others may be used as a mixture in place of or in addition to Sodium Carbonate or mixture of Sodium Carbonate ($Na_2CO_3$) and Barium Carbonate in a second solid electrolyte layer.

Figure 3:
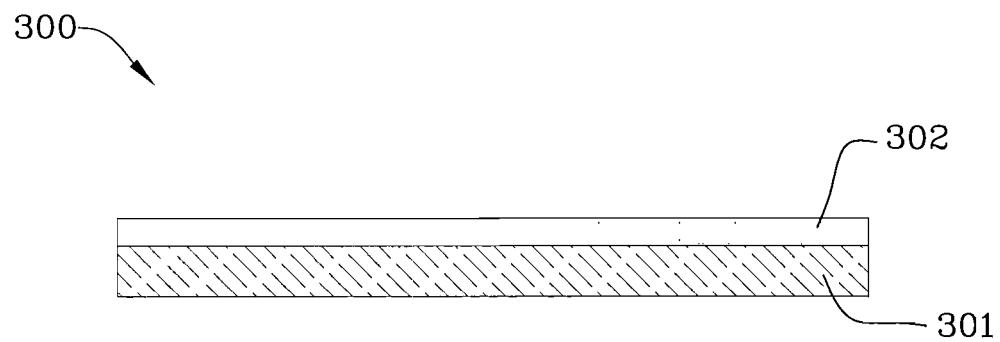
FIG. 3 is a cross-sectional schematic illustration of a substrate with photoresist spun onto the substrate.
Figure 3A:
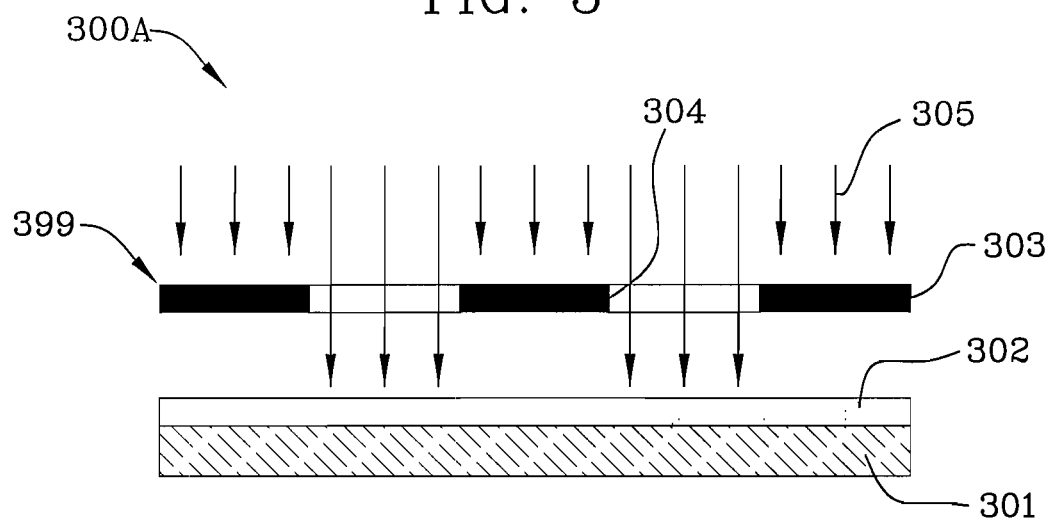
FIG. 3A is a cross-sectional schematic illustration of the substrate as illustrated in FIG. 3 with a photomask oriented thereover and ultraviolet light imidizing the unmasked portions of the photoresist.

FIG. 3 is a cross-sectional schematic illustration 300 of a substrate 301 with photoresist 302 spun onto the substrate 301. FIG. 3A is a cross-sectional schematic illustration 300A of the substrate 301 as illustrated in FIG. 3 with a photomask 399 oriented thereover and ultraviolet light 305 imidizing the unmasked portions of the photoresist. The photomask 399 includes apertures 304 and opaque portions 303.

Figure 3B:
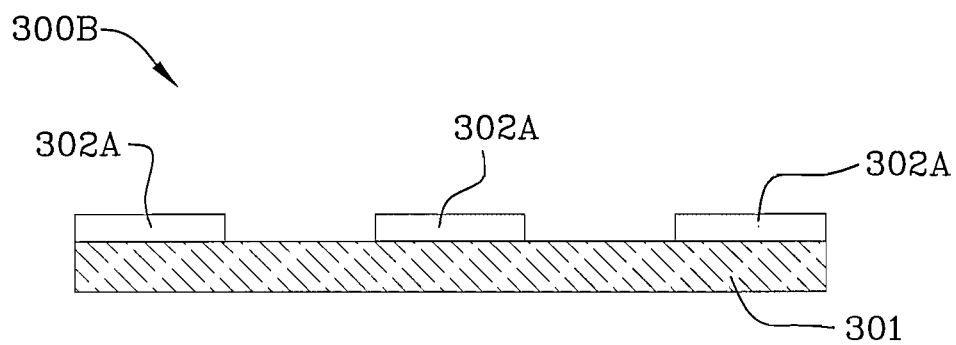
FIG. 3B is a cross-sectional schematic illustration of the substrate illustrated in FIG. 3A with the imidized photoresist developed and removed.

FIG. 3B is a cross-sectional schematic illustration 300B of the substrate 301 illustrated in FIG. 3A with the imidized photoresist developed and removed. The imidized portion of the photoresist is the portion which has been exposed to the ultraviolet light. Unimidized portions 302A of the photoresist remain on the substrate at this step.

FIG. 3C is a cross-sectional schematic illustration 300C similar to FIG. 3B with a first layer of titanium 303 sputtered onto the substrate 301 and the unimidized photoresist 302A.

FIG. 3D is an enlargement 300D of a portion of FIG. 3C illustrating the sputter deposition of the first layer of the Titanium 303A over the substrate 301 and the photoresist 302A. Titanium layer 303A is approximately 50 Å thick and forms a good bond to the Alumina substrate which is approximately 250-625 μm thick. Overall, the dimensions of the interdigitated area on the Alumina substrate is approximately 1.1 mm long, 1.0 mm wide and 250 or 625 μm thick in this embodiment of the invention. FIG. 3E is a cross-sectional schematic illustration 300E of a second layer of Platinum 304A deposited above the first metallization layer of Titanium 303A and the unimidized photoresist 302A.

FIG. 3F is a cross-sectional schematic illustration 300F of the Alumina substrate 301 with two interdigitated electrodes 304A/303A affixed to the substrate with the unimidized photoresist 302A removed with acetone or some other suitable solvent.

Figure 3H:
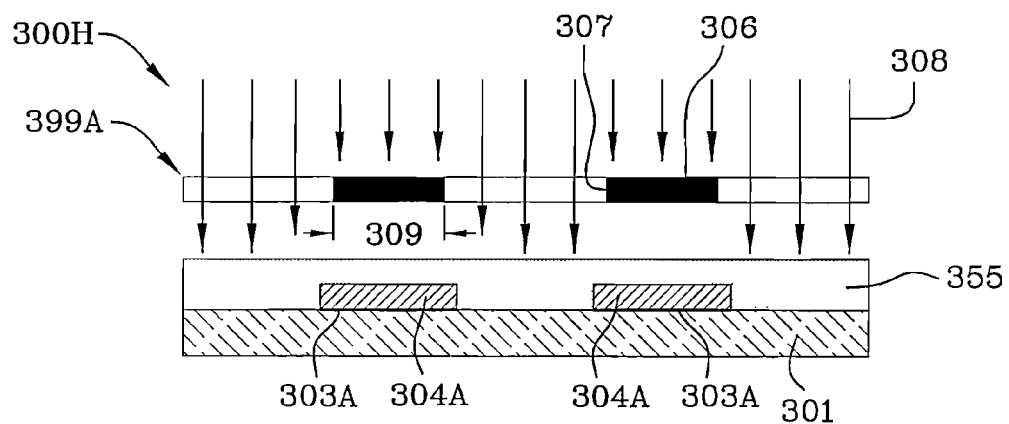
FIG. 3H is a cross-sectional schematic illustration of a mask applied to the substrate and ultra violet light imidizing the unmasked portions of the photoresist.
Figure 3I:
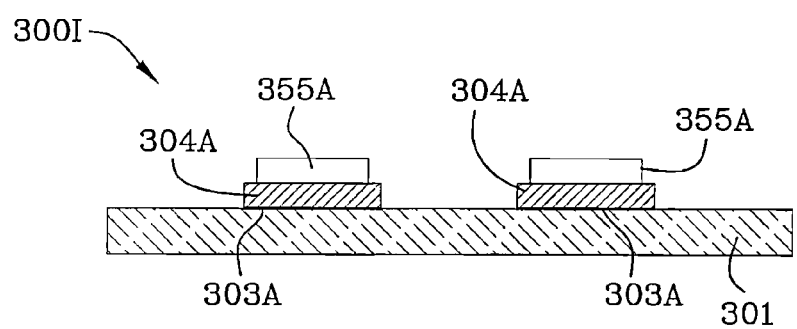
FIG. 3I is a cross-sectional schematic illustration of the substrate, interdigitated electrodes and photoresist left after the imidized photoresist has been developed and removed.

FIG. 3G is a cross-sectional schematic illustration 300G of photoresist 355 spun over the interdigitated Titanium/Platinum electrodes 304A/303A and the Alumina substrate 301. Next, FIG. 3H is a cross-sectional schematic illustration 300 H of a photomask 399A spaced apart and in proximity to the substrate 301 with interdigitated electrodes 304A/303A thereon and ultra violet light 308 passing through apertures 307 imidizing the unmasked (exposed) portions of the photoresist. Reference numeral 309 represents the width of opaque portion 306 of photomask 399A. This width is specifically designed to be less than the width of 303A/304A. Once imidization of the photoresist 355 is complete the imidized portions of the photoresist are subjected to developer and removed leaving the structure in FIG. 3I. FIG. 3I is a cross-sectional schematic illustration 300I of the substrate, interdigitated electrodes 303A/304A and unimidized photoresist 355A left after the imidized photoresist has been developed and removed.

Figure 3J:
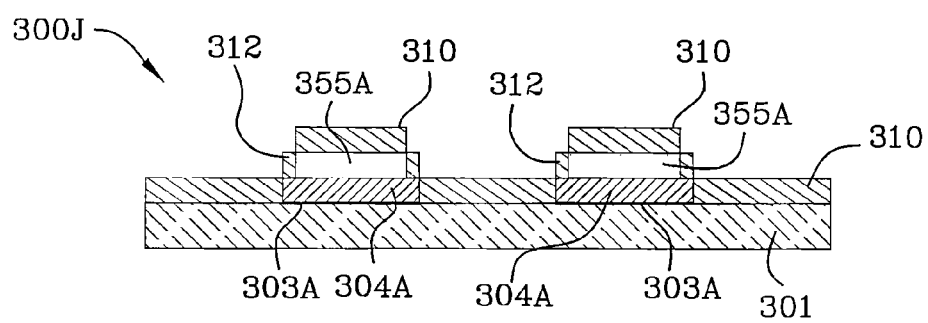
FIG. 3J is a cross-sectional schematic illustration of the substrate, interdigitated electrodes with photoresist residing on a portion thereof with a layer of a first solid electrolyte deposited thereover

Next, FIG. 3J is a cross-sectional schematic illustration 300J of the substrate 301, interdigitated electrodes 304A/303A with unimidized photoresist residing on a portion thereof with a layer of first solid electrolyte 310, for example, NASICON, deposited thereover. Reference numeral 312 indicates the portion where the NASICON is raised slightly as its deposition by E-beam evaporation follows the contour of the substrate 301, the electrodes 303A/304A and the unimidized photoresist 355A. NASICON 310 is applied at a thickness approximately equal to the thickness of the electrodes 303A/304A. E-beam deposition is used here as an example of very controlled, exact deposition of component layers providing nearly vertical deposition geometries. Actual applications may vary. In the examples set forth herein (drawing FIGS. 3-3R) one of the electrodes 303A/304A is the working electrode and the other electrode is the reference electrode. As indicated in connection with FIGS. 2-2B above, there may be 8 to 10 pairs of working and reference electrodes which combine in an interdigitated fashion to generate enough current to produce sufficient sensitivity of the sensor. Other numbers of pairs may be used. The number of electrode pairs used in a sensor depends upon the application.

Figure 3K:
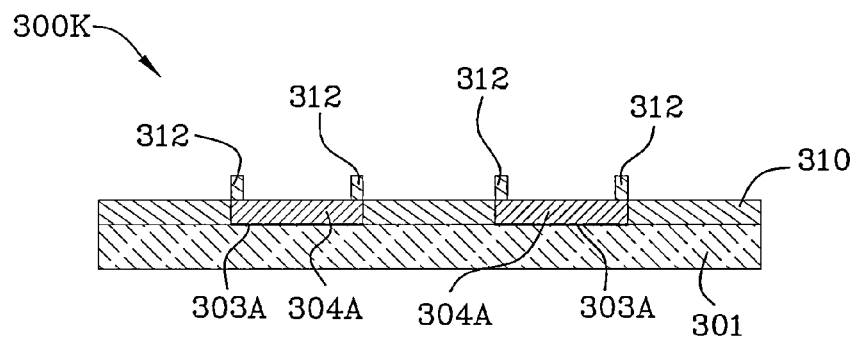
FIG. 3K is a cross-sectional schematic illustration wherein the photoresist has been removed with acetone or other suitable solvent.

FIG. 3K is a cross-sectional schematic illustration 300K wherein the unimidized photoresist 355A has been removed with acetone, or some other suitable solvent leaving a contoured surface of NASICON and Platinum electrodes exposed.

Figure 3L:
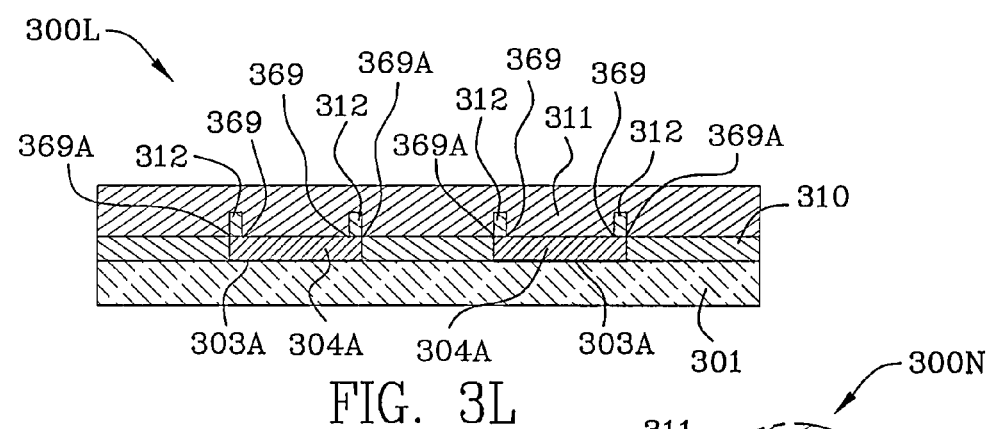
FIG. 3L is a cross-sectional schematic illustration with a second solid electrolyte deposited thereover.

FIG. 3L is a cross-sectional schematic illustration 300L with a second solid electrolyte 311 deposited over the NASICON 310 and the electrodes 303A/304A. The second solid electrolyte may be Sodium Carbonate ($Na_2CO_3$), or a combination of Sodium Carbonate ($Na_2CO_3$) and Barium Carbonate ($BaCO_3$) thereof in addition to other solid electrolytes and combinations which may include $Li_2CO_3$, $K_2CO_3$, $Rb_2CO_3$, $SrCO_3$, $Ag_2CO_3$, and $PbCO_3$. The second electrolyte layer with $Na_2CO_3$ and $BaCO_3$ mixture performs a barrier function in that it keeps the sensor less vulnerable to humidity. Further, it selectively reacts with Carbon Dioxide at the three point contacts NASICON 310, the electrode 303A/304A, and the Sodium Carbonate or mixture of Sodium Carbonate and Barium Carbonate. As described elsewhere herein, each electrode joins the NASICON and the Sodium Carbonate or mixture of Sodium Carbonate and Barium Carbonate along a line where reduction and oxidation takes place. Current flow takes place through the NASICON. Reference numeral 369 represents inboard lines of three point contact of the electrodes 303A/404A, NASICON 312, and second electrolyte Sodium Carbonate 311. Reference numeral 369A represents outboard lines of three point contact of the electrodes 303A/404A, NASICON 312, and second electrolyte Sodium Carbonate 311. Depending on the process used for applying the NASICON, the outboard lines 369A may not exist. Such is the case when the NASICON is applied by sputtering as set forth in FIG. 3"O" to FIG. 3R, inclusive.

Figure 3N:
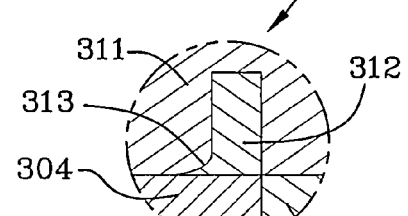
FIG. 3N is an enlargement of a portion of FIG. 3M.
Figure 3M:
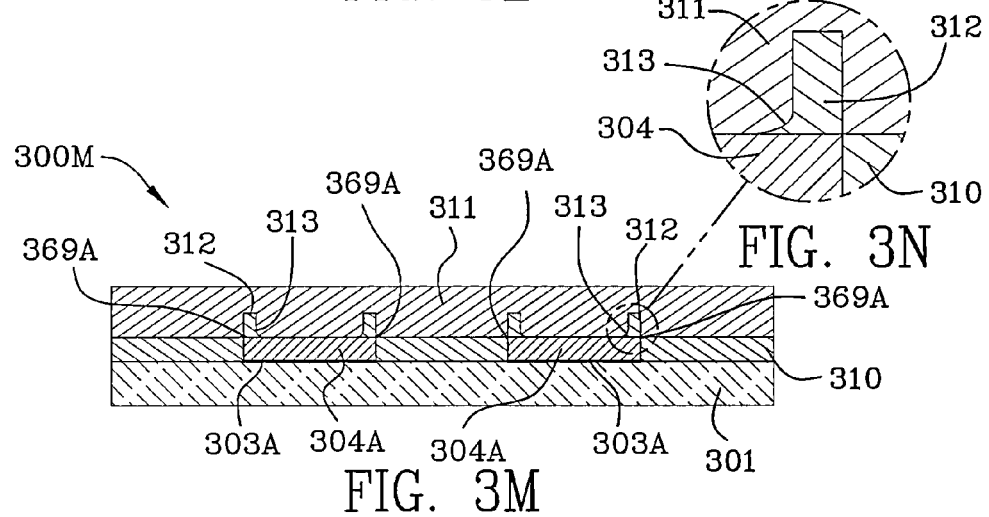
FIG. 3M is a cross-sectional schematic illustration similar to FIG. 3L wherein the electrodes form tapered surfaces at the place of joinder with the electrolytes.

FIG. 3M is a cross-sectional schematic illustration 300M similar to FIG. 3L wherein the NASICON 310, 312 includes tapered surfaces 313 at the joinder of the Platinum electrodes and the Sodium Carbonate/Barium Carbonate ($Na_2CO_3$/$BaCO_3$) layer 311. The tapered surfaces of NASICON are very thin which in effect creates several lines of multiple three point contacts which facilitates the reduction and oxidation processes set forth below. FIG. 3N is an enlargement 300N of a portion of FIG. 3M and provides a better view of the tapered surface 313, the electrode 304A, first electrolyte 312 and secondary electrolyte 311. It is believed that the tapered surface 313 plays an important role in that it provides a better amperometric surface as the NASICON layer in the tapered surface 313 is very thin resulting in multiple lines where three (3) point contacts between the electrode, NASICON, and the auxiliary Sodium Carbonate/Barium Carbonate ($Na_2CO_3$/$BaCO_3$) electrolyte layer exist.

Still referring to FIG. 3M it is believed that the tapered surfaces 313 are created as a result of heat treatment of the NASICON film at temperature as high as 850° C.

The detection system depicted in FIGS. 2-2B and 3-3R includes pairs of electrodes with constant voltage, V, applied across the multiple interdigitated electrodes.

The sensing mechanism of the amperometric $CO_2$ sensors can be understood based on the reactions taking place at the working and reference electrode of each pair of electrodes. The following two electrode reactions may be considered:

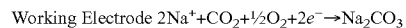
Working Electrode $2Na^+ + CO_2 + \frac{1}{2}O_2 + 2e^- \rightarrow Na_2CO_3$

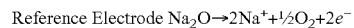
Reference Electrode $Na_2O \rightarrow 2Na^+ + \frac{1}{2}O_2 + 2e^-$ Reduction occurs as the result of the reaction taking place at the working electrode where electrons are consumed. Oxidation occurs as the result of the reaction taking place at the reference electrode where electrons are released.

The following overall reaction can then be considered to be:

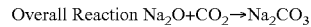
Overall Reaction $Na_2O + CO_2 \rightarrow Na_2CO_3$

Platinum is used as the preferred material for the electrode. However, electrodes made from other metals such as Palladium, Silver, Iridium, Gold, Ruthenium, Rhodium, Indium, or Osmium may also be used. In addition, non-porous or porous electrodes may be used The auxiliary electrolyte ($Na_2CO_3$ and/or $BaCO_3$ and/or $Li_2CO_3$, $K_2CO_3$, $Rb_2CO_3$, $SrCO_3$, $Ag_2CO_3$, $PbCO_3$) is deposited homogeneously on the entire sensing area of the sensor, including both the working and reference electrodes. The deposition of an auxiliary carbonate electrolyte improves flow of the desired species within the electrolyte. At the working electrode, depleted concentration of sodium ions ($Na^+$) can be recovered by the transfer of sodium ions ($Na^+$) from NASICON through the three-phase boundary of the electrodes, NASICON electrolyte, and an auxiliary electrolyte layer. The sodium carbonate, $Na_2CO_3$, deposited at the working electrode can be transferred to the reference electrode through the $Na_2CO_3$ auxiliary carbonate electrolyte if temperatures are high enough, for example, 450-600° C.

These mechanisms allow the sensor to measure $CO_2$ but recover back to its initial state. The sensing mechanism has increased performance from the $Na_2CO_3/BaCO_3$ auxiliary carbonate electrolyte layer being distributed across both the working and the reference electrodes at high operating temperatures in the 450-600° C. The eutectic mixture of $Na_2CO_3/BaCO_3$ as the auxiliary carbonate electrolyte layer has a lower melting temperature enabling improved flow within the electrolyte at a reduced temperature range. The $Na_2CO_3/BaCO_3$ auxiliary carbonate electrolyte can act as a diffusion barrier to prevent other species from reaching the electrode/electrolyte interface and interfering with the correlation of measured current with detection of the desired chemical species.

FIG. 3 "O" is a cross-sectional schematic 300 "O" similar to FIG. 3J and is another example of the application of a first solid electrolyte 310A applied over the substrate 301, interdigitated electrodes 303A/304A and unimidized photoresist 305A using sputter deposition. Sputter deposition of NASICON 310A results in a surface 320 which is contoured and does not follow the underlying components. Sputter deposition is used here as an example of a less exact, more diffuse deposition of component layers providing more graded deposition geometries. Actual applications may vary. In FIG. 3J, the NASICON was applied in a manner which results in the NASICON applied so as to more closely follow the contour of the underlying structure. Reference numeral 325 is used to indicate the NASICON above the unimidized photoresist 305A.

Figures 3P, 3Q, 3R:
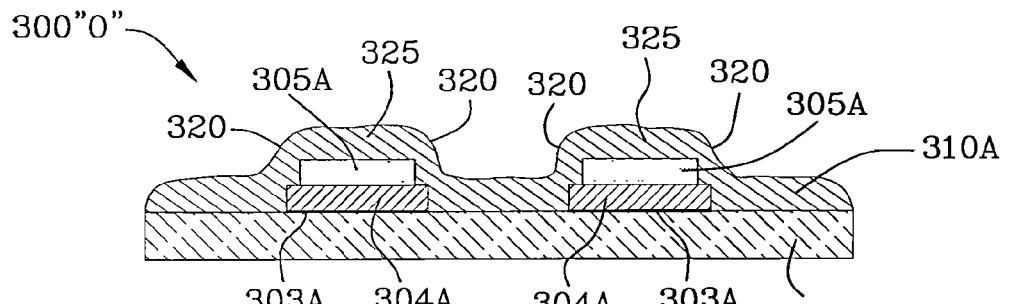
FIG. 3P is a cross-sectional schematic illustration similar to FIG. 3K wherein the photoresist has been removed with acetone or other suitable solvent.
FIG. 3Q is a cross-sectional schematic having a second solid electrolyte applied over the first solid electrolyte and the interdigitated electrodes.
FIG. 3R is a cross-sectional schematic illustration wherein a third layer, a metal oxide layer, is applied over the second solid electrolyte.

FIG. 3P is a cross-sectional schematic illustration 300P similar to FIG. 3K wherein the unimidized photoresist 305A has been removed with acetone or other suitable solvent leaving NASICON 310A behind with a contoured surface 320. Next, the auxiliary Sodium Carbonate/Barium Carbonate ($Na_2CO_3/BaCO_3$) electrolyte composition is applied. FIG. 3Q is a cross-sectional schematic 300Q having a second solid electrolyte 311 applied over the first solid electrolyte 310A and the interdigitated electrodes 303A/304A.

Figure 9:
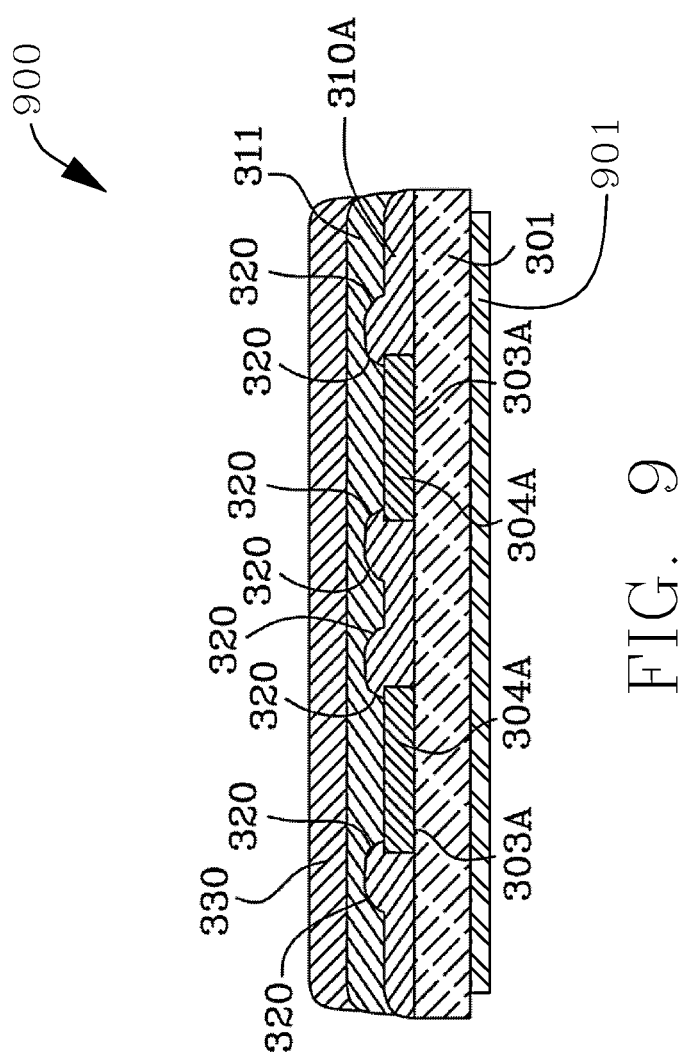
FIG. 9 is a view similar to that of FIG. 3R, a cross-sectional schematic illustration wherein a third layer, a metal oxide layer, is applied over the second solid electrolyte, and a heating element is schematically shown.

FIG. 3R is a cross-sectional schematic illustration 300R wherein a solid metal oxide 330, $SnO_2$, CuO, $In_2O_3$, and $TiO_2$ and/or a combination thereof, is applied over the second solid electrolyte 311. It is preferred that these solid metal oxides be composed of nanoparticles. In this continuation-in-part application, metal oxide(s) are represented herein using reference numeral 330, for example, $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, or $HfO_3$ can be applied over the top of or can be mixed with $Na_2CO_3/BaCO_3$ to improve sensor performance and/or to reduce sensor heating power consumption as illustrated in FIG. 3R or FIG. 9. FIG. 9 is a view similar to that of FIG. 3R, a cross-sectional schematic illustration wherein a third layer, a metal oxide layer, is applied over the second solid electrolyte, and a heating element 901 is schematically shown. The heating element controls the operational temperature of the sensor and may have the same energy source 222 as the sensor as illustrated, for example, in FIG. 2. The heating element 901 schematically illustrated in FIG. 9 is on the reverse side of the substrate and comprises resistive traces which are heated by using current to pass through the traces and heating the substrate.

Use of this third layer of metal oxide 330 provides enhanced performance of the sensor. This third layer of metal oxide 330 is applied by drop deposition of the metal oxide $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, $HfO_3$ and/or a combination thereof in the form of sol gel on top of the $Na_2CO_3/BaCO_3$ and heat treat the sensor in the instant invention. The sensor is preferably heated to a temperature of 600° C. for a period of time. The third metal oxide or any combination thereof or any catalyst defined hereinbelow can also be deposited using e-beam evaporation or sputtering using a shadow mask which is the same as that for $Na_2CO_3/BaCO_3$ deposition. The third layer of metal oxide 330 or combination thereof improves the sensor signal greatly and also enables the carbon dioxide sensor to function in a temperature range as low as 200° C.-355° C.

CuO has been determined to be sensitive in the detection of carbon dioxide gas in connection with sensors made of copper oxide and SnO2 mixture and used as a resistor. CuO may be mixed with metal oxides $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ for use as the extra layer which covers the auxiliary electrolyte. Any combination of the aforesaid metal oxides may be mixed with each other.

Any one or more catalytic metals Ru, Rh, Pd, Os, Ir, Pt, Au, Ag, W, V, Nb, Ta, Cr, Mo, Cu, Fe, Mn, Co, Ni, Ti, Zn, Cd or their alloys may be used with the metal oxides $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ or with metal oxide mixtures of $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$. All of the above chemical elements can be applied via sol gel deposition, sputtering, evaporation, or screen printing processes.

Any one or more of the metal oxides $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, $HfO_3$, and $HfO_3$ may be used and mixed with the auxiliary electrolytes barium carbonate or sodium carbonate. The aforesaid catalytic metals may also be used and mixed with the aforesaid metal oxides used wither with the carbonates or on top of and in engagement with the carbonates.

Figure 4:
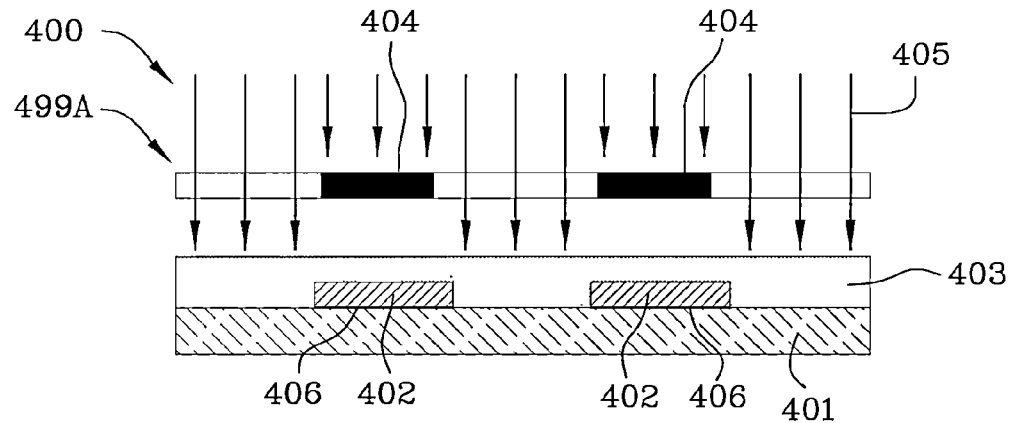
FIG. 4 is a schematic illustration similar to FIG. 3H with the mask slightly misaligned.

FIG. 4 is a schematic illustration 400 similar to FIG. 3H with the photomask 499A slightly misaligned. FIGS. 4-4D are illustrative of the fault tolerance of the instant invention. It is this fault tolerance which enables successful production of the device. The opaque portion 404 of the mask 499A is indicated with reference numeral 404 and the ultra violet light 405 is indicated with reference numeral 405. Still referring to FIG. 4, it can be seen as is discussed elsewhere herein that if the opaque portions 404 of the photomask 499A are the same width as the underlying electrodes 402/406 and they are misaligned, then a faulty sensor will result. For this reason it is necessary that the opaque portions of the mask have a width less than 30 μm and preferably in the range of 15-20 μm. Misalignment of the photomask 499A (serpentine) results in decentralized unimidized photoresist 403A. However, because the opaque portions of the mask have a width significantly smaller than the width of the electrodes perfect alignment is not necessary. The NASICON lip shown by reference numeral 412 and the NASICON indicated by reference numeral 313 are locations where the NASICON may be thin and in effect leads to more reaction sites close to three boundary contacts. Also, this speeds up the manufacturing process because the technician does not have to be perfect in alignment. This is in contrast to standard industry practice which emphasizes increasing tight alignment and deposition procedures; the approach here is to allow and in fact take advantage of diffuse deposition and inexact alignments to improve the sensor response. In the example of FIG. 4, reference numeral 406 is the thin layer (50A) of Titanium as previously described in connection with reference numeral 303A in FIGS. 3-3R. Reference numeral 402 is the relatively thicker layer (4000A) of Platinum as previously described in connection with reference numeral 304A in FIGS. 3-3R.

Figure 1:
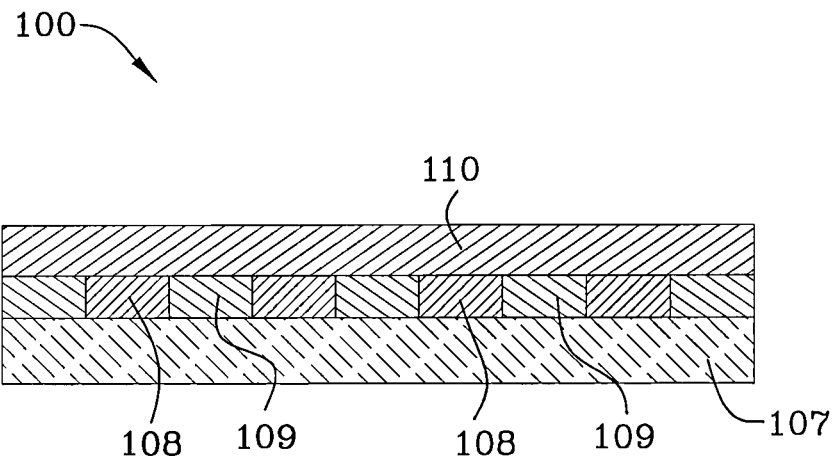
FIG. 1 is a cross-sectional schematic illustration of a prior art gas sensor.
Figure 1A:
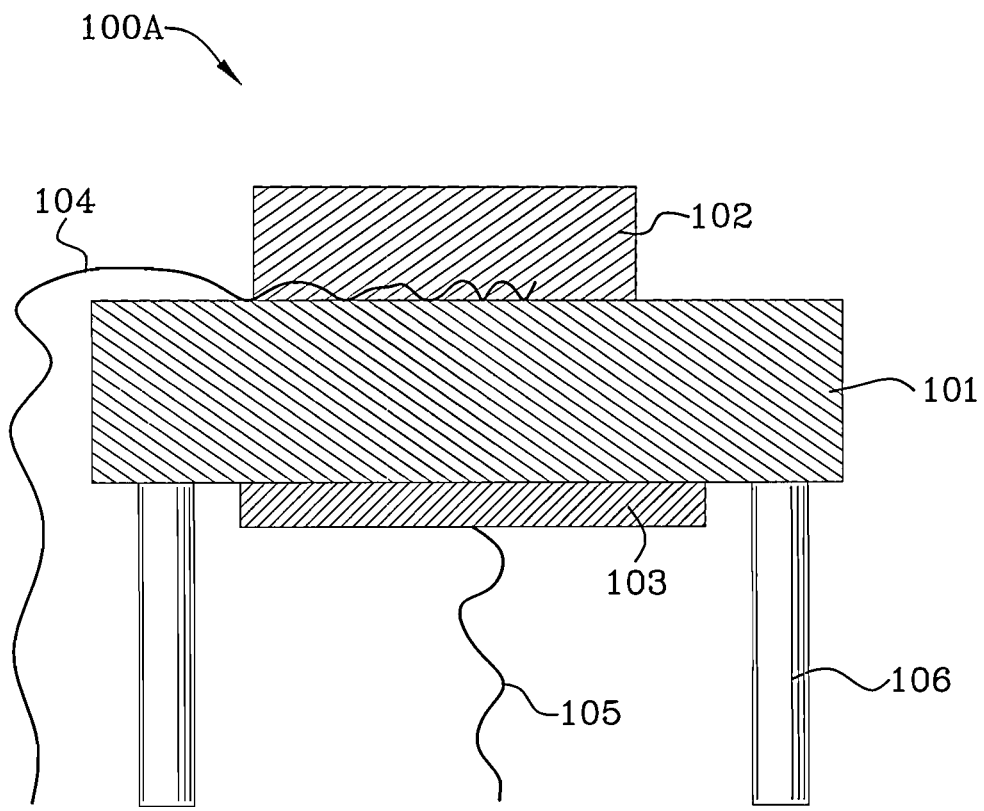
FIG. 1A is a cross-sectional schematic illustration of a prior art bulk gas sensor.
Figure 4A:
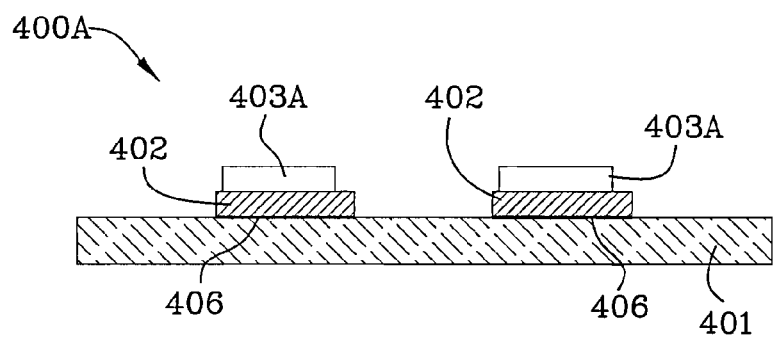
FIG. 4A is a schematic illustration of the photoresist developed and removed with photoresist remaining over the interdigitated electrodes but not centrally located (misaligned).
Figure 4B:
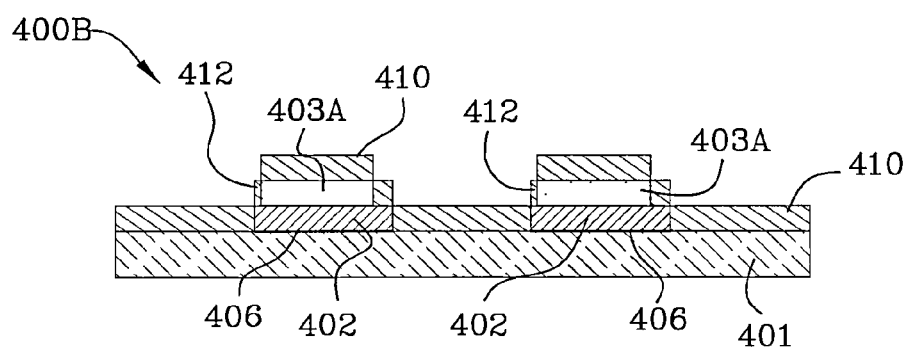
FIG. 4B is a schematic illustration similar to FIG. 4A with a first solid electrolyte deposited thereover.
Figure 4C:
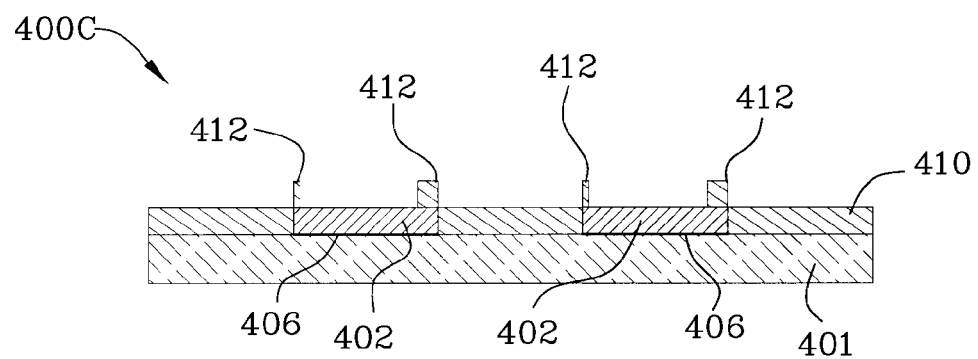
FIG. 4C is a schematic illustration with the photoresist lifted off through dissolution with acetone.
Figure 4D:
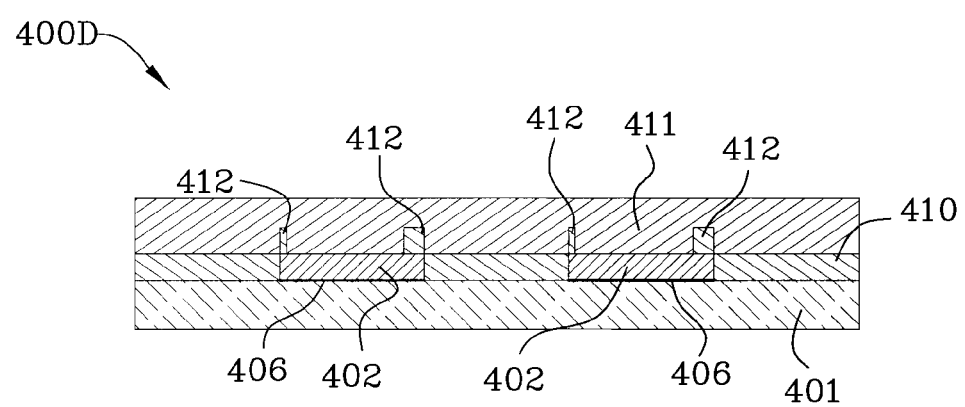
FIG. 4D is a schematic illustration similar to FIG. 4C with a second solid electrolyte deposited over the first solid electrolyte and the interdigitated electrodes.

FIG. 4A is a schematic illustration 400A of the photoresist developed and removed with unimidized photoresist 403A remaining over the interdigitated electrodes but not centrally located (misaligned). FIG. 4B is a schematic illustration similar 400B to FIG. 4A with a first solid electrolyte such as NASICON or LISICON 410 deposited thereover by e-beam evaporation. FIG. 4C is a schematic illustration 400C with the photoresist lifted off through dissolution with acetone or other suitable solvent. Raised portions of the NASICON or LISICON 410 are viewed well in FIG. 4C. FIG. 4D is a schematic illustration 400D similar to FIG. 4C with a second solid electrolyte 411 (Barium Carbonate and/or Sodium Carbonate) deposited over the first solid electrolyte and the interdigitated electrodes. FIG. 4D illustrates the potential problem with misalignment discussed elsewhere herein particularly in describing FIG. 1 which can not be produced because of the stack-up of manufacturing tolerances.

Figure 5:
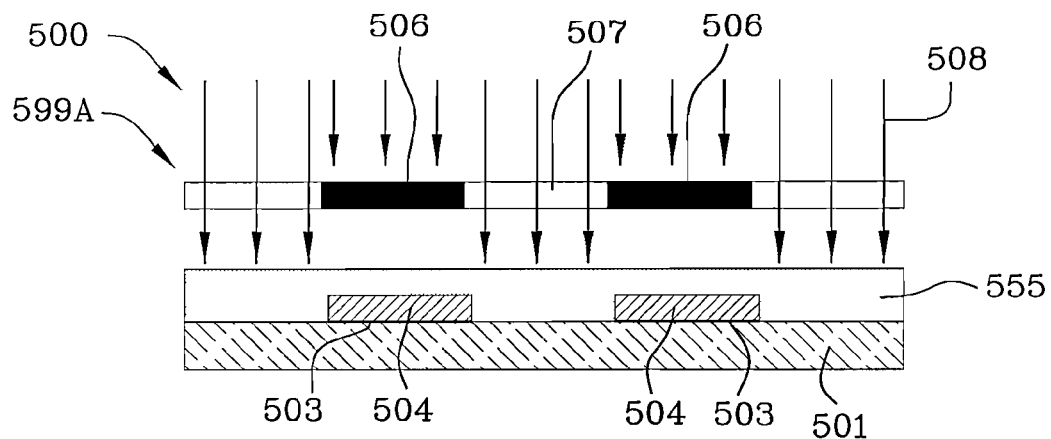
FIG. 5 is a schematic illustration similar to FIG. 4 with the mask misaligned above the substrate, interdigitated electrodes, and photoresist indicating the application of ultraviolet light thereto.

FIG. 5 is a schematic illustration 500 similar to FIG. 4 with the photomask 599A significantly misaligned above the substrate 501, interdigitated electrodes 503/504, and photoresist 555 indicating the application of ultraviolet 508 light thereto. Reference numeral 503 is the Titanium layer of the electrode and reference numeral 504 is the Platinum layer of the electrode as described and similarly proportioned to the other examples given herein. Opaque portions of the photomask 599A are indicated by reference numeral 506 and apertures in the mask are denoted by reference numeral 507. Misalignment should not occur when the opaque portions 506 of the photomask 599A are substantially smaller than the width of the electrodes as described herein. However, the illustration of FIG. 5 is being made to demonstrate that a problem is more likely to occur when the mask width equals the width of the electrodes as is the standard industry practice and direction. As the width of the opaque portion of the photomask increases or approximates the width of the electrode, the probability of misalignment increases. As was the case of the examples illustrated in FIGS. 3-3R and 4-4D, the opaque portion 506 of the mask protects the underlying photoresist and prevents ultraviolet light from reaching the photoresist resulting in a portion of the photoresist being unimidized 555A.

Figure 5A:
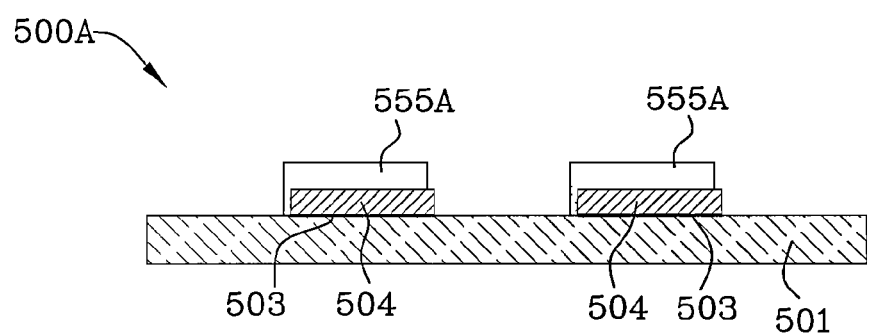
FIG. 5A is a schematic illustration similar to FIG. 5 with the imidized photoresist developed and removed leaving a gap filled with photoresist adjacent the electrodes.

FIG. 5A is a schematic illustration 500A similar to FIG. 5 with the imidized photoresist developed and removed leaving a gap filled with unimidized photoresist 555A appearing just to the left of the electrodes 503/504. This photoresist 555A which lies next to the electrodes 503/504 will interfere with the proper function of the electrodes as it prevents the joinder of the electrodes, NASICON, and the Carbonate layer as illustrated in FIG. 5D. It also blocks the movement of Na ion in NASICON between reference electrode and working electrode, which is also a critical factor for sensor to work or function.

Figure 5B:
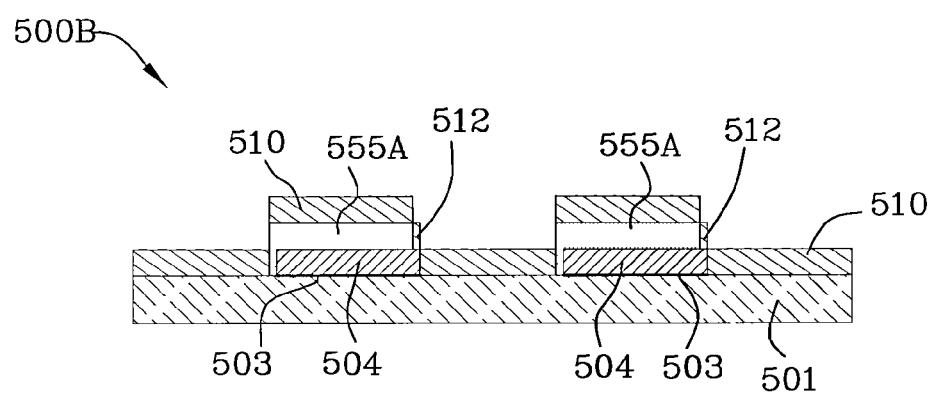
FIG. 5B is a schematic illustration with a first electrolyte over the substrate, interdigitated electrodes and photoresist.
Figure 5C:
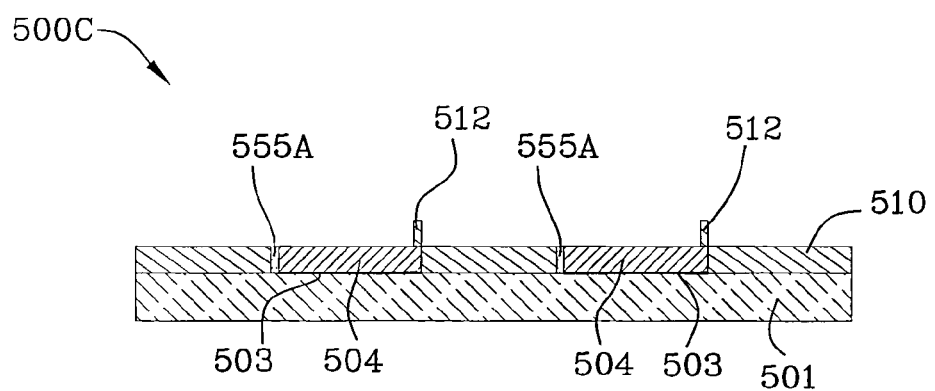
FIG. 5C is a schematic illustration similar to FIG. 5B with the photoresist lifted off.
Figure 5D:
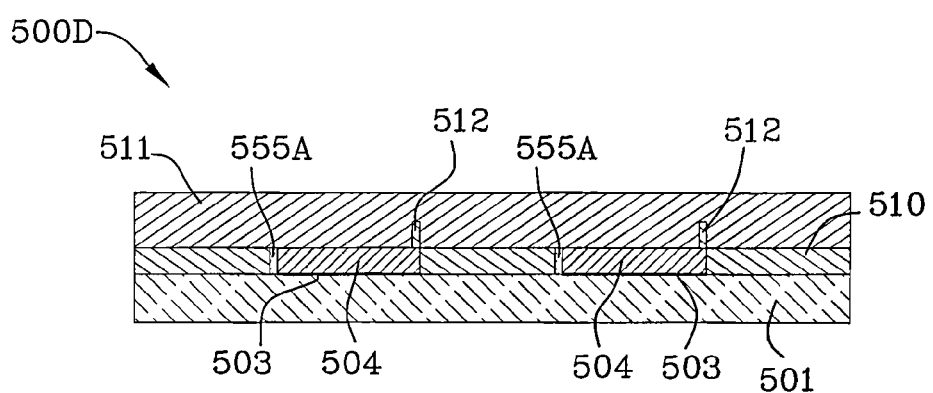
FIG. 5D is a schematic illustration similar to FIG. 5C with a second electrolyte over the first electrode and interdigitated electrodes.

FIG. 5B is a schematic illustration 500B with a first electrolyte NASICON deposited by e-beam deposition over the substrate, interdigitated electrodes, and photoresist. It will be noticed that the NASICON 510 does not abut the electrodes 503/504 on the left hand side of FIG. 5B. FIG. 5C is a schematic illustration 500C similar to FIG. 5B with the unimidized photoresist 555A lifted off with acetone. NASICON 510 includes a raised portion 512. FIG. 5D is a schematic illustration 500D similar to FIG. 5C with a second electrolyte 511 over the first electrolyte and the interdigitated electrodes 503/504.

In describing the success or failure of the carbon dioxide sensor the electrodes are interdigitated and may involve 8-10 pairs of electrodes in order to sum enough current to provide the desired sensitivity. Currents ranging from nano to micro amps are generated by the application of 1.0 Volts or higher dc across the sensor electrode bus as illustrated schematically in FIG. 2.

The fabrication of carbon dioxide sensors includes three steps: 1) Deposition of platinum interdigitated finger electrodes on Alumina substrates; 2) Deposition of solid electrolyte called NASICON ($Na_3Zr_2Si_2PO_{12}$) or LISICON ($Li_3Zr_2Si_2PO_{12}$) between the finger electrodes; and 3) Deposition of auxiliary electrolytes sodium carbonate and/or barium carbonate ($Na_2CO_3/BaCO_3$, 1:1.7 in molar ratio for the combination) on the upper surfaces of the electrodes.

The Platinum interdigitated finger electrodes were deposited as follows: Alumina substrates (250 μm or 625 μm in thickness) were patterned with photoresist and an interdigitated finger electrode photomask. A 50 Å layer of Titanium and a 4000 Å layer of Platinum were deposited on the Alumina substrate by sputter deposition. After development and removal, the substrates were then patterned again to cover the top of interdigitated finger electrodes with photoresist.

Deposition of the NASICON solid electrolyte between the finger electrodes and the $Na_2CO_3/BaCO_3$ was performed as follows. The solid electrolyte NASICON was deposited by e-beam evaporation or sputtering. A liftoff process which uses acetone to remove unimidized photoresist was conducted to remove NASICON on the upper surfaces of the electrodes resulting in the NASICON mainly staying between the interdigitated finger electrodes and exposing most of the electrode surface. The substrate was heated in an oven at 850° C. for 2 hours. $Na_2CO_3/BaCO_3$ (1:1.7 in molar ratio) was then deposited on the upper surfaces of the electrodes and the NASICON surface by sputtering using a shadow mask. The use of shadow mask in this step is to prevent the Na ion in deposited NASION being washed away by photolithograph process, which is not obvious and not a typical practice of standard microfabrication process. The substrates were heated in an oven at 686° C. for 10 minutes and 710° C. for 20 minutes. Different concentrations of carbon dioxide gases were tested by the sensors at temperatures ranging from 450-600° C. The sensor was tested by applying a voltage to the electrodes and measuring the resulting current. A linear response to carbon dioxide concentrations between 1% to 4% was achieved. Linear responses of the natural logarithmic of carbon dioxide concentrations between 0.02% to 1% was achieved.

The resulting miniature $CO_2$ sensor can be integrated into a sensor array with other sensors and electronics, power, and telemetry on a stamp sized package. Like a postage stamp, the complete system (lick and stick technology) can be placed at a number of locations including some hidden areas to give a full-field understanding of what is occurring in an environment. The same sensor structure could also be applied to develop $NO_x$ or $SO_x$ with the corresponding auxiliary electrolytes $NaNO_2$ and $NaNO_3$, or $Na_2CO_3$ and $Na_2SO_4$.

Figure 6:
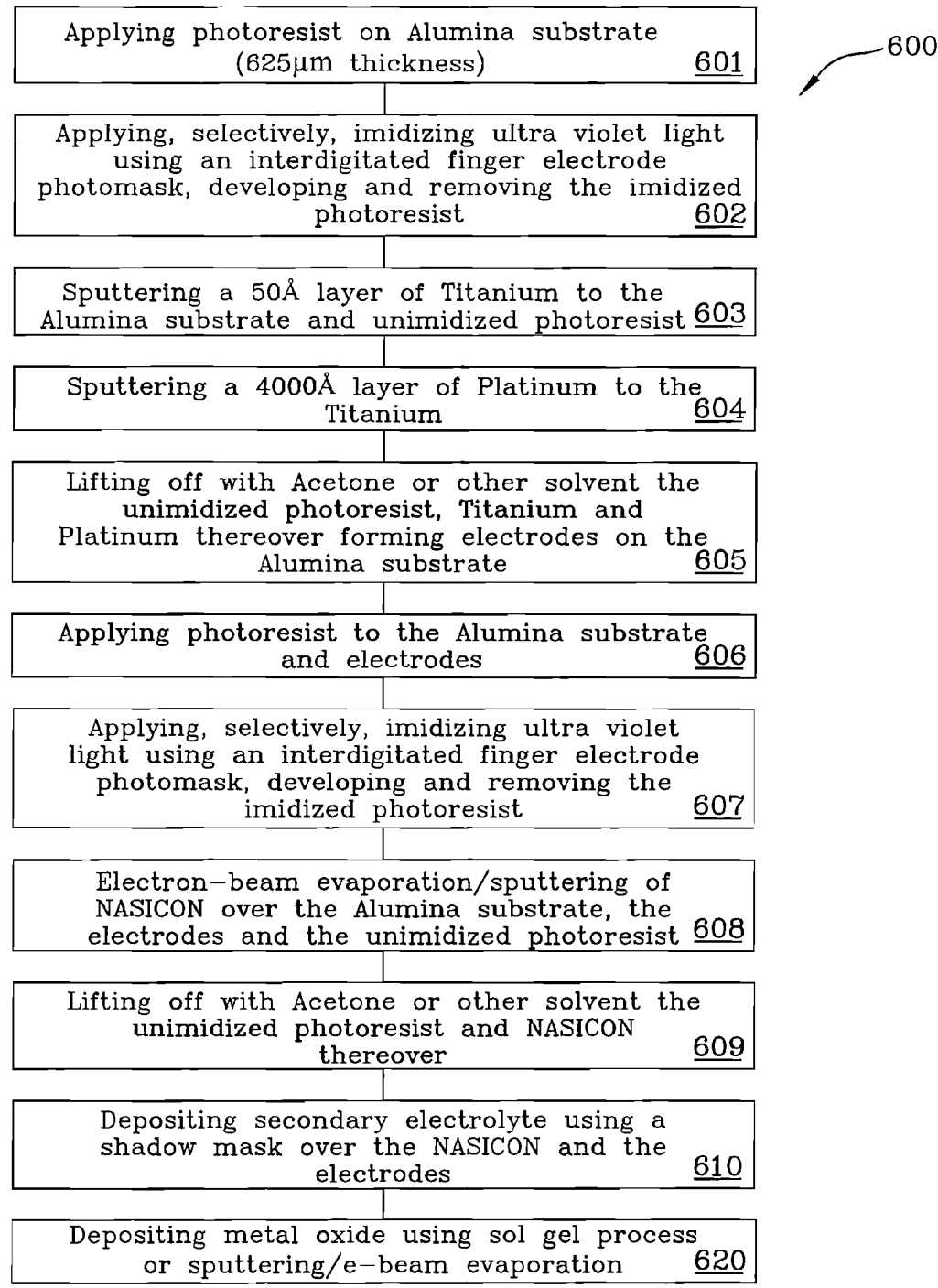
FIG. 6 is a schematic illustration of one example of process steps used to make the sensors.

FIG. 6 is a schematic illustration 600 of one example of process steps used to make the sensors. The process steps are described below and have been described hereinabove.

First, an Alumina substrate is coated with photoresist 302. A photomask 399 is then applied selectively 602 imidizing ultra violet light using an interdigitated finger electrode photomask and developing and removing the imidized photoresist. Next, sputtering 603, a 50 Å layer of Titanium 303A onto the Alumina 301 substrate and unimidized photoresist 302A is performed. The sputtering of the Titanium is followed by sputtering 604 a 4000 Å layer of Platinum onto the Titanium.

The unimidized photoresist 302A is lifted off 605 with acetone or other solvent to remove the unimidized photoresist 302A as well as the Titanium 303A and Platinum 304A thereover forming electrodes on the Alumina substrate. Another layer of photoresist is then applied 606 to the Alumina substrate 301 and electrodes 303A/304A. The photoresist is selectively imidized 607 by applying imidizing ultraviolet light 308 using an interdigitated finger electrode photomask 399A and then developing and removing the imidized photoresist. Electron beam evaporation or sputtering 608 of NASICON over the Alumina substrate, the electrodes and the unimidized photoresist follows. Lifting off 609 the unimidized photoresist and NASICON thereover with acetone or other solvent is then performed so as to enable the deposition of secondary electrolyte 610 using a shadow mask over the NASICON and the electrodes. The step 620 of depositing a metal oxide may be accomplished by drop deposition of metal oxide sol gel or by sputtering/e-beam deposition using a shadow mask.

Figure 7:
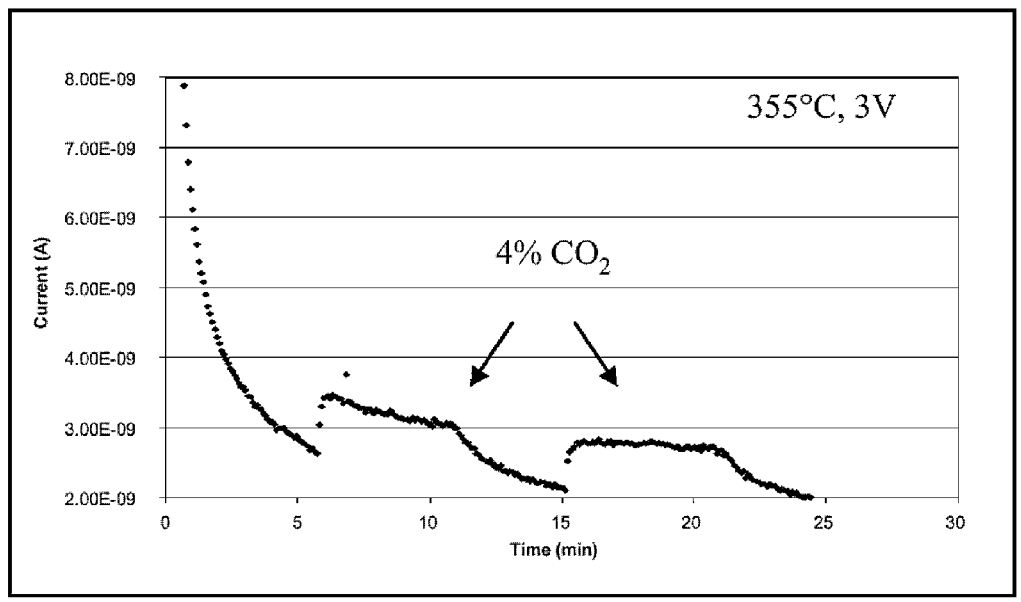
FIG. 7 is a plot of current generated by the sensor as a function of time at 355° C. at 3 Volts DC without the addition of tin oxide gel.

FIG. 7 is a plot 700 of current generated by the sensor subjected to 4% $CO_2$ as a function of time with operation at 355° C., and with 3 Volts DC across the platinum electrodes, and without the addition of tin oxide gel over the carbonate layer. The sensor structure is set forth in FIG. 3Q. Three (3) volts dc is applied across the platinum contacts 304A. Also see FIG. 2 wherein the voltage of battery 222 is applied across contacts 201/207 which is schematically representative of applying the voltage across the contacts. Carbon dioxide gas ($CO_2$) with a concentration of 4% by weight was applied to the sensor for 5 minutes and then the sensor was subjected to air for the following 5 minutes. The cycle was repeated.

Figure 7A:
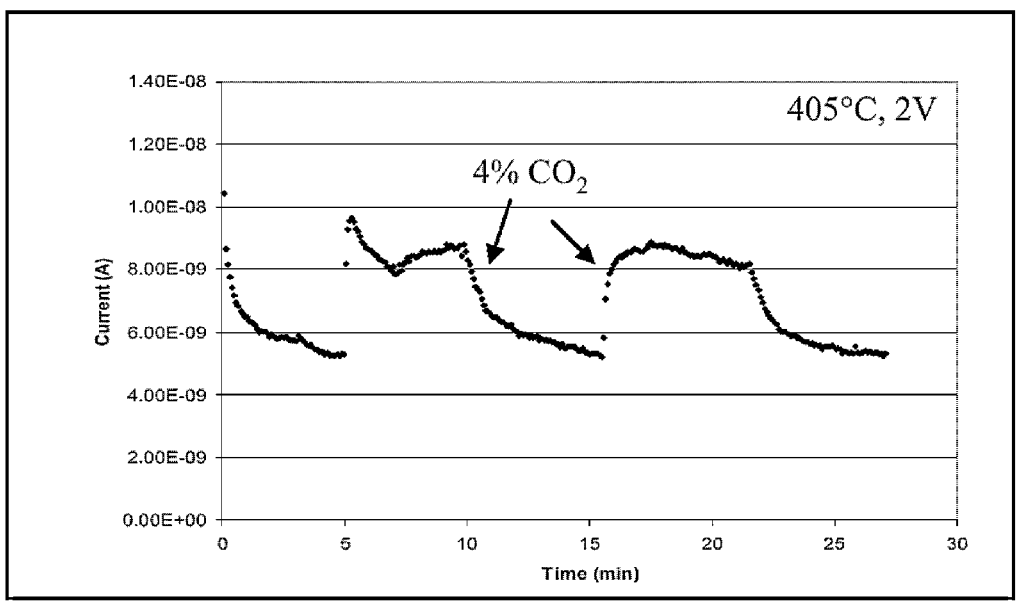
FIG. 7A is a plot of current generated by the sensor without the tin oxide at 405° C. at 2 Volts DC.

FIG. 7A is a plot 700A of current generated by the sensor subjected to 4% $CO_2$ without the tin oxide applied over and in engagement with the carbonate layer 311 with operation at 405° C. with 2 Volts DC impressed across the platinum electrodes 304A. Carbon dioxide gas ($CO_2$) with a concentration of 4% by weight was applied to the sensor for 5 minutes and then the sensor was subjected to air for the following 5 minutes. The cycle was repeated.

Figure 8:
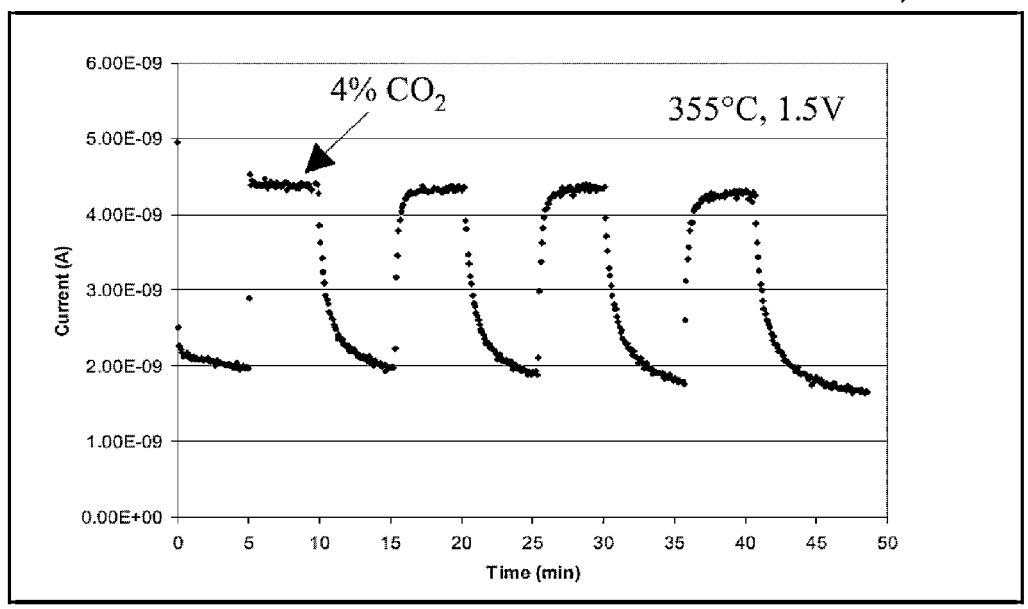
FIG. 8 is a plot of current generated by the sensor after tin oxide sol gel at 355° C. at 1.5 Volts DC.

FIG. 8 is a plot 800 of current generated by the sensor subjected to 4% $CO_2$ after tin oxide sol gel was added over the carbonate layer 311 with operation at 355° C. and with 1.5 Volts dc impressed across the platinum electrodes thereof. Carbon dioxide gas ($CO_2$) with a concentration of 4% by weight was applied to the sensor for 5 minutes and then the sensor was subjected to air for the following 5 minutes. The cycle was repeated.

Figure 8A:
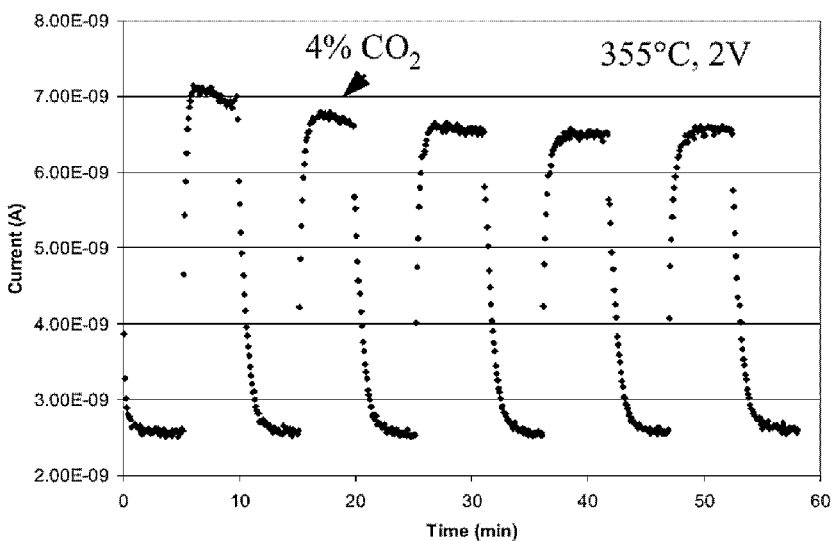
FIG. 8A is a plot of current generated by the sensor after tin oxide sol gel at 355° C. at 2 Volts DC.

FIG. 8A is a plot 800A of current generated by the sensor subjected to 4% $CO_2$ after tin oxide sol gel was added over the carbonate layer 311 with operation at 355° C. and with 2 Volts dc impressed across the platinum electrodes thereof. Electrons or holes are applied to the sensor from the $SnO_2$, $In_2O_3$, $TiO_2$, $WO_3$, ZnO, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CuO, $Cu_2O$, SnO, NiO, $Pr_2O_3$, BaO, $PdO_2$, $HfO_3$, and $HfO_3$ through the carbonate layer and to the three point contact of the NASICON, the platinum electrodes and carbonate which facilitates the redox at a lower temperature (energy level). Thus, less energy is supplied to the heater 901 on the back side of the substrate as set forth schematically in FIG. 9.

The plots of current versus time in FIGS. 8 and 8A indicate better resolution, to with, a large maximum current to a relatively small minimum current as compared with FIGS. 7 and 7A. The best illustration is a comparison of FIGS. 7A and 8A wherein 2 Volts dc is applied across the electrodes 304A. The resolution of FIG. 7A shows step changes of about 6 E-9 to 9E-9. Under similar conditions the resolution of FIG. 8A indicates step changes of 2.5 E-9 to 6.5E-9. Better resolution at lower temperature is illustrated in FIG. 8A at a lower temperature of 355° C. (FIG. 8A) vs. 405° C. (FIG. 7A). FIGS. 7A and 8A indicate the application of an atmosphere containing 4% concentration of $CO_2$ by weight applied to the sensor for 5 minutes followed by a 5 minute period wherein the sensor is subject to air. The cycle is repeated as indicated by the plots.

FIG. 9 is a view 900 similar to that of FIG. 3R, a cross-sectional schematic illustration wherein a third layer, a metal oxide layer, is applied over the second solid electrolyte, and a heating element 901 is schematically shown.

Figure 10:
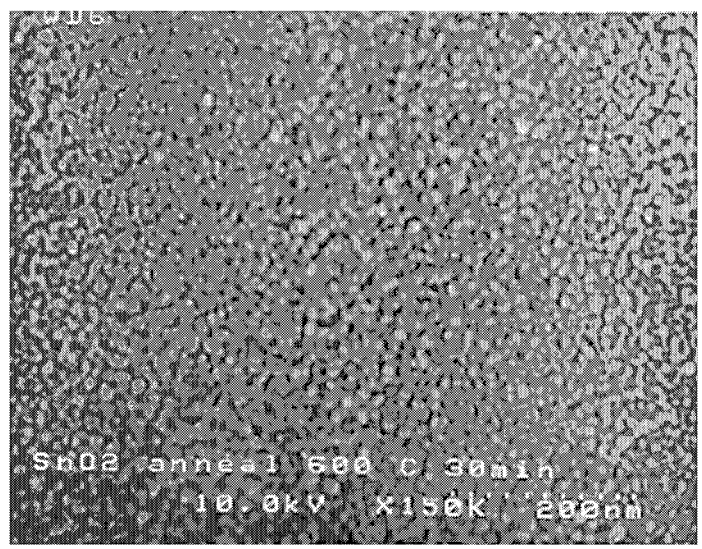
FIG. 10 is a micro photograph of Nanocystalline $SnO_x$ deposited by the sol gel process.

FIG. 10 is a micro photograph 1001 of Nanocystalline SnO, deposited by the sol gel process.

REFERENCE NUMERALS

100—schematic of prior art device
100A—schematic of prior art device
101—NASICON
102, 110—Sodium Carbonate/Barium Carbonate ($Na_2CO_3$/$BaCO_3$)
103—Platinum paste
104—sensing electrode
105—reference electrode
106—quartz glass tube
107—Alumina
108—interdigitated Platinum metal electrodes
109—NASICON
200—schematic of interdigitated metal electrodes
200A—schematic view of section 2A-2A
200B—view of section 2A-2A with NASICON and Barium Carbonate/Sodium Carbonate thereover
201—contact pad
202—lead
203—positive bus
204—interdigitated positive metal electrodes
205—gap between electrodes
206, 301—substrate (insulator)
207—contact pad
208—lead
209—negative bus
210—interdigitated negative metal electrodes
211—width of gap between electrodes
212—contour of NASICON after liftoff of photoresist
212W—width of electrode
213—thin layer of Titanium metal
220—amp meter
221—conductor
222—battery or electrical potential 300—schematic view of substrate with photoresist spun thereover
300A—schematic view of mask over substrate with photoresist spun thereover
300B—schematic view of substrate with imidized photoresist developed and removed
300C—schematic view of substrate and unimidized photoresist with a thin layer of Titanium thereover
300D—enlargement of a portion of FIG. 3C
300E—schematic view of second metal layer of Platinum applied over the first metal layer of Titanium
300F—schematic view of interdigitated electrodes and substrate after liftoff of photoresist
300G—schematic view of photoresist spun over the interdigitated electrodes and substrate
300H—schematic view of mask placed over photoresist
300I—schematic view of substrate, electrodes and unimidized photoresist after the imidized photoresist has been developed and removed
300J—schematic view of NASICON deposited by e-beam evaporation over the substrate, electrodes, and photoresist
300K—schematic view with the photoresist lifted off
300L—schematic view similar to FIG. 3K with a second electrolyte deposited over the NASICON and electrodes
300M—schematic view of another example of the invention wherein multiple three point contacts occur between the NASICON, the electrodes and the second electrolyte
300N—schematic view of an enlargement of a portion of FIG. 3M
300 "O"—schematic view similar to FIG. 3J wherein NASICON is sputtered over the substrate, electrode and the photoresist
300P—schematic view similar to FIG. 3K wherein the unimidized photoresist has been lifted off
300Q—schematic view a second electrolyte sputtered, using a shadow mask, over the NASICON and electrodes
300R—schematic view of a third electrolyte sputtered, using a shadow mask, over the second electrolyte
301, 401, 501—Alumina, substrate (non-conductive)
302, 355, 403, 555—photoresist
302A, 305A, 355A, 403A, 555A—unimidized photoresist
305, 308, 405, 508—UV light
303, 306, 404, 506—opaques portions of photomask
303A, 406, 503—thin first Titanium metal layer
304, 307, 507—aperture in mask
304A, 402, 504—second Platinum metal layer
305, 308—ultraviolet light
309—width of opaque portion of mask
310, 410, 510—NASICON, first solid electrolyte, e-beam deposited
310A—NASICON, first solid electrolyte, sputter deposited
311, 411, 511—second solid electrolyte Sodium Carbonate/Barium Carbonate ($Na_2CO_3/BaCO_3$)
312, 412, 512—raised portion of NASICON
313—extended three-point contact
320—contour of sputter deposited NASICON
325—sputter deposited NASICON
330—layer of metal oxide, $SnO_2$, $CuO$, and $TiO_2$.
369—inboard three point electrical contact
369A—outboard three point electrical contact
399, 399A, 499A, 599A—photomask
400—schematic view similar to FIG. 3H with the mask slightly misaligned although still over the electrodes electrolyte is sputter deposited over the NASICON and electrodes
400A—schematic view similar to FIG. 3I with the imidized photoresist developed and removed
400B—schematic view similar to FIG. 3J with NASICON deposited by e-beam evaporation over the substrate, electrodes and unimidized photoresist
400C—schematic view similar to FIG. 3K with the unimidized Photoresist lifted off
400D—schematic view similar to FIG. 3L schematic illustration similar to FIG. 4C with a second solid electrolyte deposited over the first solid electrolyte and the interdigitated electrodes.
500—schematic view similar to FIG. 4 with the mask misaligned
500A—schematic view similar to FIG. 4A with the unimidized photoresist extending beyond the electrodes
500B—schematic view similar to FIG. 4B with NASICON deposited over the substrate, unimidized photoresist and electrodes.
500C—schematic view similar to FIG. 4C with the unimidized photoresist developed and removed.
500D—schematic view similar to FIG. 4D with a second solid electrolyte deposited over the NASICON, unimidized photoresist and metal electrodes
600—one example of process steps used to fabricate the sensor
601—applying photoresist on Alumina substrate
602—applying, selectively, imidizing ultra violet light using an interdigitated finger electrode photomask, developing and removing the imidized photoresist
603—sputtering a 50 Å layer of Titanium onto the Alumina substrate and unimidized photoresist
604—sputtering a 4000 Å layer of Platinum onto the Titanium
605—lifting off with acetone or other solvent the unimidized photoresist, Titanium and Platinum thereover forming electrodes on the Alumina substrate
606—applying photoresist to the Alumina substrate and electrodes
607—applying, selectively, imidizing ultraviolet light using an interdigitated finger electrode photomask, developing and removing the imidized photoresist
608—electron beam sputtering of NASICON over the Alumina substrate, the electrodes and the unimidized photoresist
609—lifting off with acetone or other solvent the unimidized photoresist and NASICON thereover
610—depositing secondary electrolyte using a shadow mask over the NASICON and the electrodes
620—depositing metal oxide using metal oxide sol gel or by sputtering/e-beam deposition
700—plot of current generated by the sensor as a function of time at 355° C. at 3 Volts DC without the addition of tin oxide gel
700A—plot of current generated by the sensor without the tin oxide at 405° C. at 2 Volts DC
800—plot of current generated by the sensor after tin oxide sol gel at 355° C. at 2 Volts DC
800A—plot of current generated by the sensor after tin oxide sol gel at 355° C. at 2 Volts DC
900—view similar to that of FIG. 3R, a cross-sectional schematic illustration wherein a third layer, a metal oxide layer, is applied over the second solid electrolyte, and a heating element is schematically shown
901—heating element
1000—micro photograph of Nanocystalline $SnO_x$ deposited by the sol gel process The invention has been set forth by way of example. Those skilled in the art will recognize that changes may be made to the invention without departing from the spirit and the scope of the claims which follow hereinbelow.

We claim:

1. A process for sensing carbon dioxide, including the following steps:
   applying a constant direct current voltage across a pair of electrodes, said electrodes being separated by an electrolyte material containing sodium, said electrodes located between a layer of Alumina substrate and a carbonate layer of auxiliary electrolyte, and, an extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, and $HfO_3$ and mixtures thereof residing above and in engagement with said auxiliary electrolyte;
   reacting carbon dioxide with said electrolyte material containing sodium at a first three-point boundary, said first three point boundary being at the joinder of one of said electrode, said electrolyte material containing sodium, and a barium containing auxiliary electrolyte;
   reacting an oxide of sodium at a second three-point boundary, said second three-point boundary being at the joinder of the other of said electrodes, said electrolyte material containing sodium, and a barium containing auxiliary electrolyte;
   measuring the resulting current; and,
   correlating change in current to the concentration of carbon dioxide.

2. A process for sensing carbon dioxide as claimed in claim 1 wherein said extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $MoO_3$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, $PdO_2$, and $HfO_3$ is mixed with said auxiliary carbonate to improve sensor performance and/or to reduce sensor heating power consumption.

3. A process for sensing carbon dioxide as claimed in claim 1 wherein said metal oxide layer or metal oxide mixtures layer further comprises a catalytic metal used in combination therewith and selected from the group consisting of Ru, Rh, Pd, Os, Ir, Pt, Au, Ag, W, V, Nb, Ta, Cr, Mo, Cu, Fe, Mn, Co, Ni, Ti, Zn, Cd or an alloy thereof.

4. A gas sensor comprising: a substrate layer; a pair of interdigitated metal electrodes each having a plurality of electrode fingers, said electrodes include upper surfaces, said electrodes, selected from the group consisting of Pt, Pd, Au, Ir, Ag, Ru, Rh, In, and Os, and alloys thereof; a first layer of solid electrolyte staying in between electrode fingers and partially on said upper surfaces of said electrodes, said first layer selected from NASICON, LISICON, KSICON, and β″-Alumina; a second layer of metal carbonate(s) as an auxiliary electrolyte engaging said upper surfaces of said electrodes and said first solid electrolyte; said metal carbonates comprise an element selected from the group consisting of the following ions $Na^+$, $K^+$, $Li^+$, $Ag^+$, $H^+$, $Pb^{2+}$, $Sr^{2+}$, $Ba^{2+}$, and any combination thereof; an extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, and $HfO_3$ and mixtures thereof residing above and in engagement with said auxiliary electrolyte to improve sensor performance and/or to reduce sensor heating power consumption.

5. A gas sensor as claimed in claim 4 wherein said extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, and $HfO_3$ is mixed with $Na_2CO_3$/$BaCO_3$ to improve sensor performance and/or to reduce sensor heating power consumption.

6. A gas sensor as claimed in claim 4 wherein said metal oxide layer or metal oxide mixtures layer further comprises a catalytic metal used in combination therewith and selected from the group consisting of Ru, Rh, Pd, Os, Ir, Pt, Au, Ag, W, V, Nb, Ta, Cr, Mo, Cu, Fe, Mn, Co, Ni, Ti, Zn, Cd or an alloy thereof.

7. A gas sensor comprising: a substrate layer; a pair of interdigitated metal electrodes each having a plurality of electrode fingers, said electrodes include upper surfaces, said electrodes, selected from the group consisting of Pt, Pd, Au, Ir, Ag, Ru, Rh, In, and Os, and alloys thereof; a first layer of solid electrolyte staying in between electrode fingers and partially on said upper surfaces of said electrodes, said first layer selected from NASICON, LISICON, KSICON, and β″-Alumina; a second layer of metal carbonate(s) as an auxiliary electrolyte engaging said upper surfaces of said electrodes and said first solid electrolyte; said metal carbonates comprise an element selected from the group consisting of the following ions $Na^+$, $K^+$, $Li^+$, $Ag^+$, $H^+$, $Pb^{2+}$, $Sr^{2+}$, $Ba^{2+}$, and any combination thereof; an extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, and $HfO_3$ and mixtures thereof mixed with $Na_2CO_3$/$BaCO_3$ and residing above and in engagement with said auxiliary electrolyte to improve sensor performance and/or to reduce sensor heating power consumption.

8. A gas sensor as claimed in claim 7 wherein said metal oxide layer or metal oxide mixtures layer further comprises a catalytic metal used in combination therewith and selected from the group consisting of Ru, Rh, Pd, Os, Ir, Pt, Au, Ag, W, V, Nb, Ta, Cr, Mo, Cu, Fe, Mn, Co, Ni, Ti, Zn, Cd or an alloy thereof.

9. A process for fabricating a carbon dioxide sensor including the following steps:
   depositing platinum interdigitated finger electrodes on a Alumina substrate, said electrodes having an upper surface;
   depositing solid electrolyte selected from the group of LISICON, KSICON, NASICON or and β″-Alumina between said finger electrodes and on a portion of said upper surface of said interdigitated finger electrodes; and,
   depositing an auxiliary electrolyte material comprising a compound selected from the group consisting of Sodium Carbonate, Barium Carbonate, and mixtures thereof on top of the electrodes; and,
   depositing an extra layer of metal oxide selected from the group consisting of $SnO_2$, $In_2O_3$, $TiO_2$, $WO_3$, $ZnO$, $Fe_2O_3$, ITO, CdO, $U_3O_8$, $Ta_2O_5$, BaO, $MoO_2$, $V_2O_5$, $Nb_2O_5$, CuO, $Cr_2O_3$, $La_2O_3$, $RuO_3$, $RuO_2$, $ReO_2$, $ReO_3$, $Ag_2O$, CoO, $Cu_2O$, SnO, NiO, $Pr_2O_3$, BaO, $PdO_2$, and $HfO_3$, and mixtures thereof residing above and in engagement with said auxiliary electrolyte to improve sensor performance and/or to reduce sensor heating power consumption.

10. A process for fabricating a carbon dioxide sensor as claimed in claim 9 wherein said metal oxide layer or metal oxide mixtures layer further comprises a catalytic metal used in combination therewith and selected from the group consisting of Ru, Rh, Pd, Os, Ir, Pt, Au, Ag, W, V, Nb, Ta, Cr, Mo, Cu, Fe, Mn, Co, Ni, Ti, Zn, Cd or an alloy thereof.

11. A process for fabricating a carbon dioxide sensor as claimed in claim 9 wherein said metal oxides are applied via sol gel deposition, sputtering, evaporation, or screen printing processes.

12. A process for fabricating a carbon dioxide sensor as claimed in claim 9 wherein said metal oxides are applied by sputtering.

13. A process for fabricating a carbon dioxide sensor as claimed in claim 9 wherein said metal oxides are applied by e-beam evaporation.

14. A process for fabricating a carbon dioxide sensor as claimed in claim 9 wherein said metal oxides are applied by screen printing.

15. A process for fabricating a carbon dioxide sensor as claimed in claim 9 wherein said step of depositing interdigitated finger electrodes includes the following steps:
    patterning said alumina substrate with photoresist and an interdigitated finger electrode photomask;
    developing and removing imidized photoresist;
    depositing a layer of 50 Å of material selected from the group consisting of Platinum Oxide and Titanium on said Alumina substrate;
    depositing a layer of 4000 Å of Platinum on said Alumina substrate;
    patterning said alumina substrates again to cover said upper surface of said interdigitated finger electrodes and said Alumina substrate with photoresist; and,
    developing and removing imidized photoresist.

16. A process for fabricating a carbon dioxide sensor as claimed in claim 15 wherein said step of depositing solid electrolyte NASICON between said finger electrodes and on a portion of said upper surface of said interdigitated finger electrodes includes the following steps:
    depositing solid NASICON over said Alumina substrate, said interdigitated finger electrodes and the unimidized photoresist;
    removing said unimidized photoresist with acetone to remove NASICON from said upper surface of said interdigitated finger electrodes exposing said upper surfaces of said interdigitated electrodes; and,
    heating said substrate in an oven at a temperature range of 850° C.

17. A process for fabricating carbon dioxide sensor as claimed in claim 16 wherein the step of the depositing an auxiliary electrolyte material comprising sodium carbonate and barium carbonate on top of the electrodes includes the steps of:
    sputtering solid auxiliary electrolyte layer between said interdigitated finger electrodes and on said NASICON using a shadow mask; and,
    heating said substrates in an oven at approximately 686° C. for 10 minutes and at approximately 710° C. for 20 minutes.

18. A process for fabricating a carbon dioxide sensor as claimed in claim 16 wherein said step of depositing solid NASICON over said Alumina substrate, said interdigitated finger electrodes and the unimidized photoresist, said NASICON solid electrolyte is deposited by e-beam evaporation.

19. A process for fabricating a carbon dioxide sensor as claimed in claim 16 wherein said step of depositing solid NASICON over said Alumina substrate, said interdigitated finger electrodes and the unimidized photoresist, said NASICON solid electrolyte is deposited by sputtering.

20. A process for fabricating a carbon dioxide sensor as claimed in claim 9 wherein said step of depositing solid electrolyte NASICON between said finger electrodes and on a portion of said upper surface of said interdigitated finger electrodes is performed by e-beam evaporation.

21. A process for fabricating a carbon dioxide sensor as claimed in claim 9 wherein said step of depositing solid electrolyte NASICON between said finger electrodes and on a portion of said upper surface of said interdigitated finger electrodes is performed by sputtering.

* * * * *